United States Patent
Meyers et al.

(10) Patent No.: US 8,177,849 B2
(45) Date of Patent: May 15, 2012

(54) METHODS AND APPARATUSES FOR ATTACHING TISSUE TO ORTHOPAEDIC IMPLANTS

(75) Inventors: John E. Meyers, Columbia City, IN (US); Robert E. Montgomery, Mishawaka, IN (US); Douglas G. Branscome, Fort Wayne, IN (US); Clarence M. Panchison, Warsaw, IN (US); Kelly A. Timmons, Warsaw, IN (US); Kimberly Les, Clarkston, MI (US); Peter E. Darrigan, Fort Wayne, IN (US); Lawrence F. Peek, Warsaw, IN (US); Ernust U. Conrad, Seattle, WA (US); Peter S. Walker, New York, NY (US); Mary I. O'Connor, Jacksonville, FL (US); Gary D. Bos, Moxee, WA (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 12/618,028

(22) Filed: Nov. 13, 2009

(65) Prior Publication Data
US 2011/0009973 A1    Jan. 13, 2011

Related U.S. Application Data

(63) Continuation-in-part of application No. 12/115,763, filed on May 6, 2008, now abandoned.

(60) Provisional application No. 60/916,414, filed on May 7, 2007.

(51) Int. Cl.
*A61F 2/38* (2006.01)

(52) U.S. Cl. .................................................. 623/20.32

(58) Field of Classification Search .... 623/20.14–20.34, 623/16.11, 11.11, 17.11–17.17, 13.11–13.18
See application file for complete search history.

(56) References Cited

U.S. PATENT DOCUMENTS

| | | | | |
|---|---|---|---|---|
| 2,719,522 A | * | 10/1955 | Hudack | 623/23.15 |
| 3,886,601 A | * | 6/1975 | Findlay | 623/20.22 |
| 4,257,129 A | * | 3/1981 | Volz | 623/20.33 |
| 4,355,427 A | * | 10/1982 | Schneider | 623/19.14 |
| 4,714,475 A | * | 12/1987 | Grundei et al. | 623/20.32 |
| 4,728,335 A | | 3/1988 | Jurgutis | |
| 4,863,474 A | | 9/1989 | Brown et al. | |
| 4,883,492 A | | 11/1989 | Frey et al. | |
| 4,969,904 A | | 11/1990 | Koch et al. | |
| 4,976,738 A | | 12/1990 | Frey et al. | |
| 4,988,351 A | | 1/1991 | Paulos et al. | |
| 5,013,324 A | | 5/1991 | Zolman et al. | |
| 5,080,674 A | | 1/1992 | Jacobs et al. | |
| 5,133,760 A | * | 7/1992 | Petersen et al. | 623/20.36 |
| 5,139,528 A | | 8/1992 | Koch et al. | |
| 5,198,308 A | | 3/1993 | Shetty et al. | |

(Continued)

OTHER PUBLICATIONS

Surgical Protocol, Stryker Orthopaedics, GMRS Proximal Tibial, Global Modular Replacement System, 2004 (GMRSSURGICAL).

(Continued)

*Primary Examiner* — Alvin J. Stewart
(74) *Attorney, Agent, or Firm* — Faegre Baker Daniels

(57) ABSTRACT

Methods and apparatuses for attaching tissue structures to orthopedic implants. In one exemplary embodiment, the methods and apparatuses are used to attach soft tissue and/or bone to a proximal tibial implant. In another exemplary embodiment, the methods and apparatuses are used to attach soft tissue and/or bone to a proximal femoral implant.

28 Claims, 29 Drawing Sheets

U.S. PATENT DOCUMENTS

| | | | |
|---|---|---|---|
| D339,634 S | 9/1993 | Hori et al. | |
| 5,314,427 A | 5/1994 | Goble et al. | |
| 5,405,396 A * | 4/1995 | Heldreth et al. | 623/20.32 |
| 5,496,375 A | 3/1996 | Sisk et al. | |
| D368,777 S | 4/1996 | Goble et al. | |
| 5,504,300 A | 4/1996 | Devanathan et al. | |
| D374,286 S | 10/1996 | Goble et al. | |
| D374,287 S | 10/1996 | Goble et al. | |
| D374,482 S | 10/1996 | Goble et al. | |
| D375,791 S | 11/1996 | Goble et al. | |
| 5,672,284 A | 9/1997 | Devanathan et al. | |
| 5,681,310 A | 10/1997 | Yuan et al. | |
| 5,725,541 A | 3/1998 | Anspach, III et al. | |
| 5,773,789 A | 6/1998 | Devanathan et al. | |
| 5,824,104 A * | 10/1998 | Tuke | 623/20.32 |
| D404,128 S | 1/1999 | Huebner | |
| D406,340 S | 3/1999 | Knoepfle | |
| 5,944,758 A | 8/1999 | Mansat et al. | |
| 5,957,979 A * | 9/1999 | Beckman et al. | 623/20.33 |
| 5,961,555 A | 10/1999 | Huebner | |
| 5,973,222 A | 10/1999 | Devanathan et al. | |
| 6,004,352 A * | 12/1999 | Buni | 623/20.33 |
| 6,039,764 A * | 3/2000 | Pottenger et al. | 623/20.32 |
| 6,049,054 A | 4/2000 | Panchison et al. | |
| 6,056,751 A | 5/2000 | Fenton, Jr. | |
| 6,080,195 A * | 6/2000 | Colleran et al. | 623/20.32 |
| 6,126,693 A * | 10/2000 | O'Neil et al. | 623/20.32 |
| 6,127,596 A | 10/2000 | Brown et al. | |
| 6,132,442 A | 10/2000 | Ferragamo et al. | |
| 6,139,581 A * | 10/2000 | Engh et al. | 623/20.34 |
| 6,193,761 B1 | 2/2001 | Treacy | |
| 6,210,444 B1 * | 4/2001 | Webster et al. | 623/20.33 |
| 6,210,445 B1 * | 4/2001 | Zawadzki | 623/20.33 |
| 6,217,619 B1 * | 4/2001 | Keller | 623/20.34 |
| 6,245,110 B1 * | 6/2001 | Grundei et al. | 623/20.31 |
| 6,283,999 B1 | 9/2001 | Rockwood, Jr. | |
| 6,296,641 B2 | 10/2001 | Burkhead et al. | |
| 6,371,985 B1 | 4/2002 | Goldberg | |
| 6,383,187 B2 | 5/2002 | Tormala et al. | |
| 6,398,812 B1 | 6/2002 | Masini | |
| 6,482,232 B1 | 11/2002 | Boucher et al. | |
| 6,520,994 B2 | 2/2003 | Nogarin | |
| 6,558,425 B2 | 5/2003 | Rockwood, Jr. | |
| 6,592,622 B1 | 7/2003 | Ferguson | |
| 6,824,566 B2 * | 11/2004 | Kana et al. | 623/20.15 |
| 6,863,072 B1 | 3/2005 | Sinnott et al. | |
| 6,866,666 B1 | 3/2005 | Sinnott et al. | |
| 6,913,623 B1 | 7/2005 | Zhu | |
| 6,953,479 B2 * | 10/2005 | Carson et al. | 623/20.15 |
| 6,986,791 B1 * | 1/2006 | Metzger | 623/20.24 |
| 7,001,429 B2 * | 2/2006 | Ferguson | 623/13.14 |
| 7,025,788 B2 * | 4/2006 | Metzger et al. | 623/20.15 |
| 7,044,973 B2 | 5/2006 | Rockwood, Jr. et al. | |
| 7,070,622 B1 * | 7/2006 | Brown et al. | 623/20.14 |
| 7,101,401 B2 * | 9/2006 | Brack | 623/20.33 |
| 7,175,664 B1 * | 2/2007 | Lakin | 623/19.14 |
| 7,179,295 B2 * | 2/2007 | Kovacevic | 623/17.15 |
| 7,211,111 B2 | 5/2007 | Boucher et | |
| 7,544,211 B2 * | 6/2009 | Rochetin | 623/20.34 |
| 7,842,093 B2 * | 11/2010 | Peters et al. | 623/20.15 |
| 2002/0151982 A1 | 10/2002 | Masini | |
| 2003/0105465 A1 | 6/2003 | Schmieding et al. | |
| 2004/0204766 A1 * | 10/2004 | Siebel | 623/20.31 |
| 2004/0215345 A1 * | 10/2004 | Perrone et al. | 623/20.32 |
| 2005/0090902 A1 | 4/2005 | Masini | |
| 2005/0177162 A1 | 8/2005 | McLeod et al. | |
| 2006/0030945 A1 * | 2/2006 | Wright | 623/20.15 |
| 2006/0178749 A1 | 8/2006 | Pendleton et al. | |
| 2006/0241776 A1 | 10/2006 | Brown et al. | |
| 2007/0093835 A1 | 4/2007 | Orbay et al. | |
| 2007/0173945 A1 | 7/2007 | Wiley et al. | |
| 2007/0179627 A1 * | 8/2007 | Gustilo et al. | 623/20.15 |
| 2007/0203499 A1 | 8/2007 | Boucher et al. | |
| 2007/0233125 A1 | 10/2007 | Wahl et al. | |
| 2007/0244565 A1 | 10/2007 | Stchur | |
| 2007/0255412 A1 | 11/2007 | Hajaj et al. | |
| 2007/0270853 A1 | 11/2007 | Leung | |
| 2008/0021566 A1 * | 1/2008 | Peters et al. | 623/20.16 |
| 2008/0133024 A1 | 6/2008 | Meswania | |
| 2008/0255622 A1 | 10/2008 | Mickiewicz et al. | |
| 2008/0281428 A1 * | 11/2008 | Meyers et al. | 623/20.35 |
| 2008/0306602 A1 * | 12/2008 | Worland et al. | 623/20.14 |
| 2010/0100190 A1 * | 4/2010 | May et al. | 623/20.14 |
| 2010/0100191 A1 * | 4/2010 | May et al. | 623/20.34 |
| 2010/0222889 A1 * | 9/2010 | Howling et al. | 623/20.21 |
| 2010/0222890 A1 * | 9/2010 | Barnett et al. | 623/20.33 |
| 2010/0298947 A1 * | 11/2010 | Unger | 623/20.32 |
| 2011/0009973 A1 * | 1/2011 | Meyers et al. | 623/20.32 |
| 2011/0029092 A1 * | 2/2011 | Deruntz et al. | 623/20.32 |
| 2011/0066246 A1 * | 3/2011 | Ries et al. | 623/20.27 |
| 2011/0066249 A1 * | 3/2011 | Justin et al. | 623/20.32 |
| 2011/0082559 A1 * | 4/2011 | Hartdegen et al. | 623/20.32 |
| 2011/0106268 A1 * | 5/2011 | Deffenbaugh et al. | 623/20.32 |
| 2011/0112650 A1 * | 5/2011 | Masini | 623/20.15 |
| 2011/0118847 A1 * | 5/2011 | Lipman et al. | 623/20.27 |
| 2011/0125283 A1 * | 5/2011 | Otto et al. | 623/20.32 |
| 2011/0202139 A1 * | 8/2011 | Metzger et al. | 623/20.28 |
| 2011/0213467 A1 * | 9/2011 | Lozier et al. | 623/20.32 |

OTHER PUBLICATIONS

Product Brochures, Stanmore Implants Worldwide Ltd., Modular Proximal Femur, Modular Distal Femur, Modular Total Femur 2001-2006 (STANMORE).

Howmedica Osteonics, Global Modular Replacement System, Product Development Limerick—Rev 2, 1 page, 1998.

Stryker, GMRS Proximal Femoral Surgical Protocol, 32 pages, Copyright 2008.

Kotz et al., "Modular replacement of femur and tibia," Supplied by the British Library, pp. 195-201, 1987.

Zimmer, MOST Options System, Surgical Technique, "Modular Options for Severe Bone Loss and Trauma," 84 pages, Copyright 2005.

Zimmer, MOST Options System, Product Brochure, "Modular Knee and Hip Options for Severe Bone Loss, Trauma and Revision," 6 pages, Copyright 2005, 2008.

DePuy, Orthogenesis Limb Preservation System, Surgical Techniques, 60 pages, Copyright 2003.

Biomet, Oncology Salvage System Overview, 158 pages, Copyright 2002.

* cited by examiner

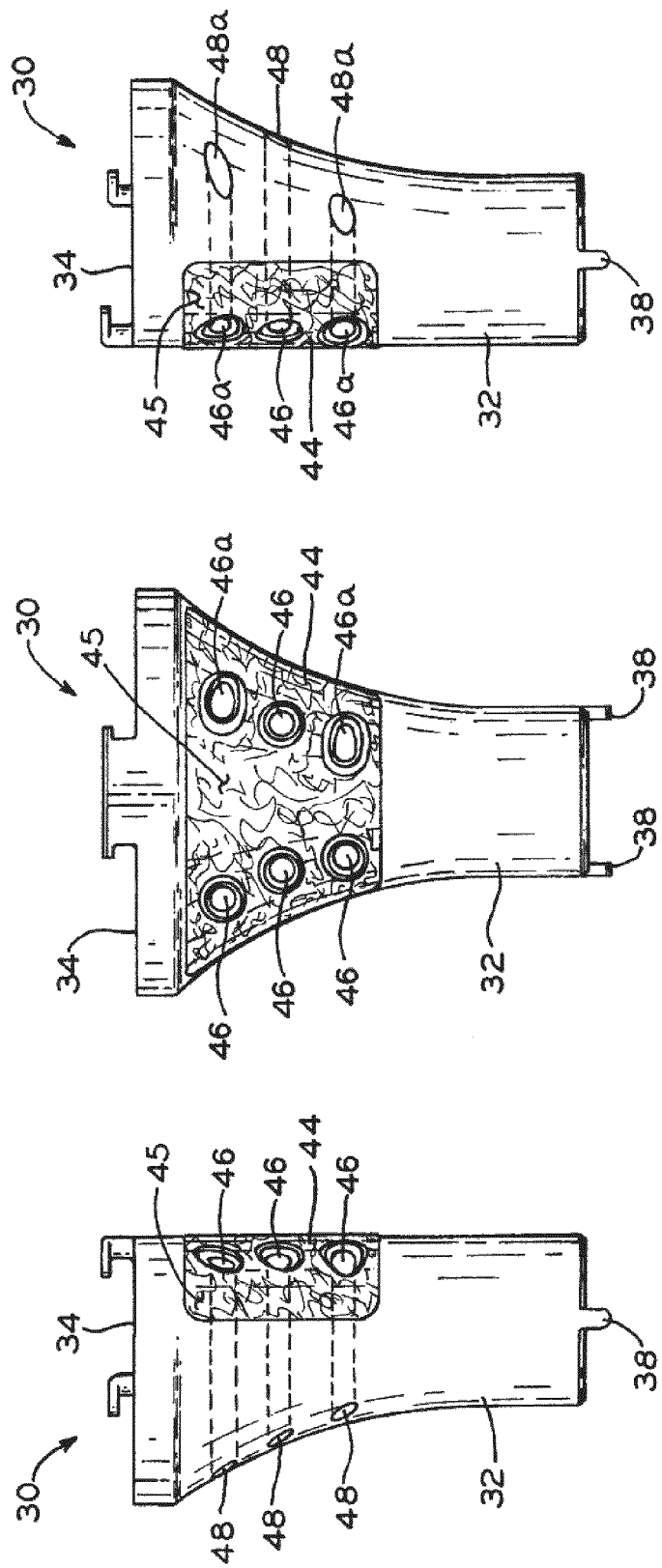

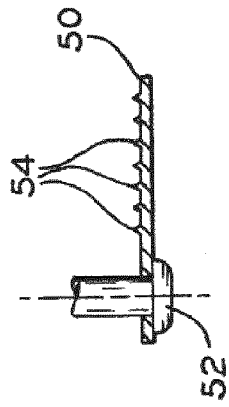
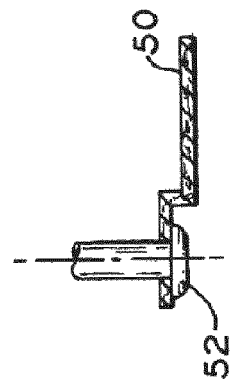
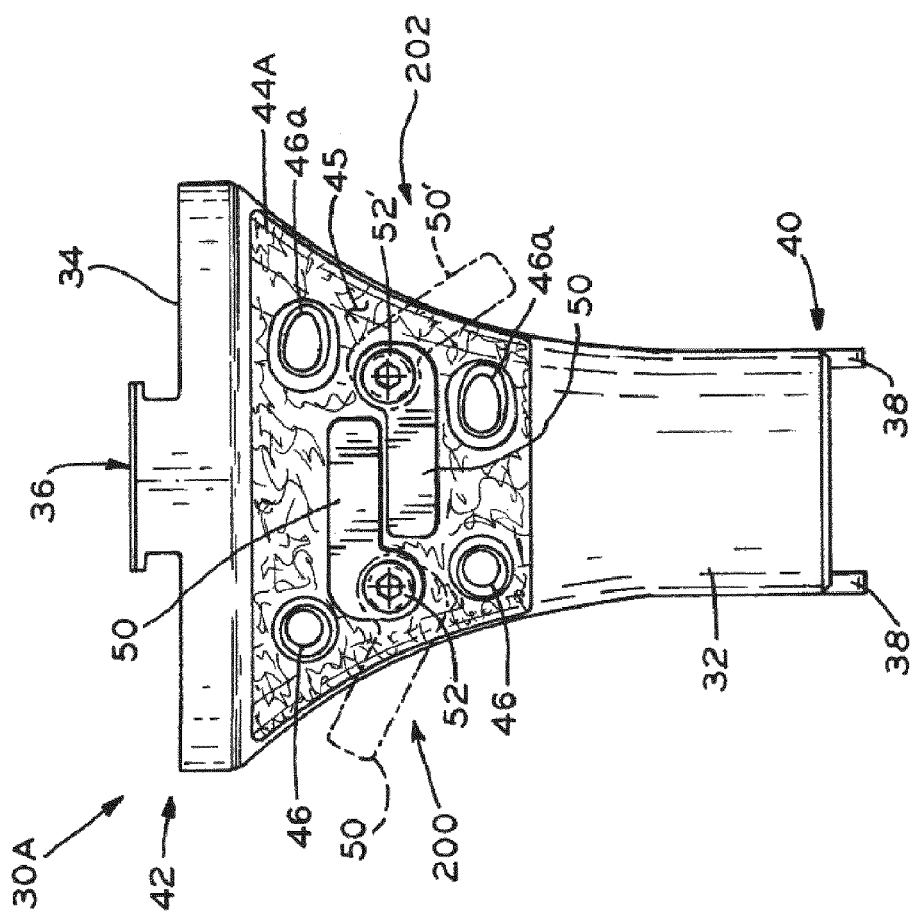

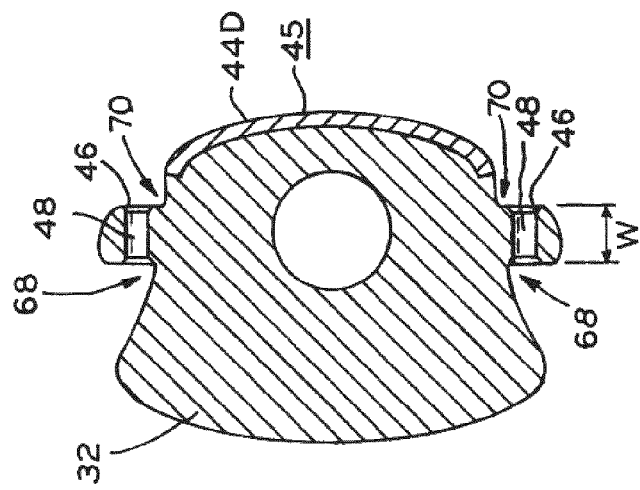
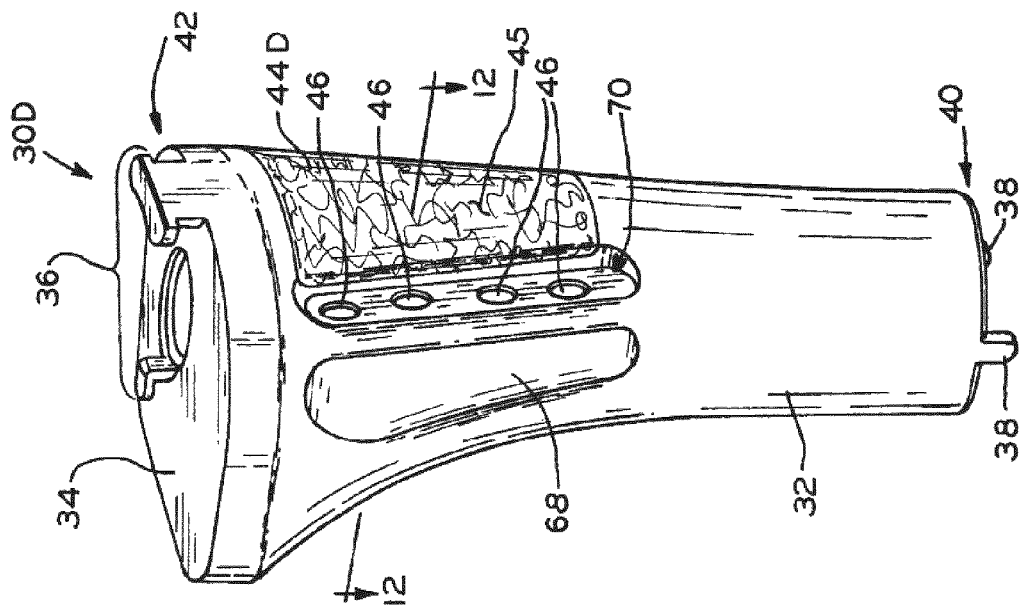

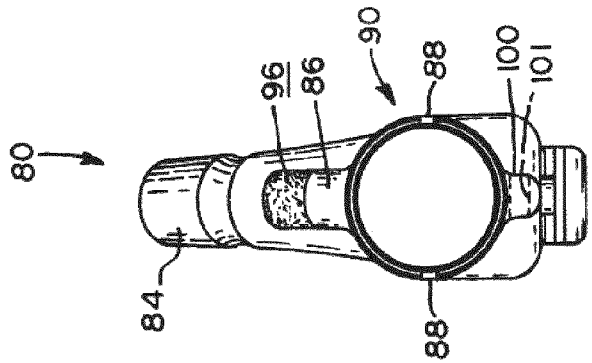
FIG_17
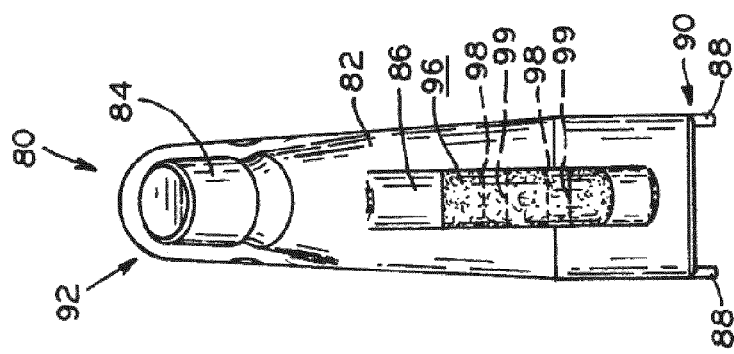
FIG_16
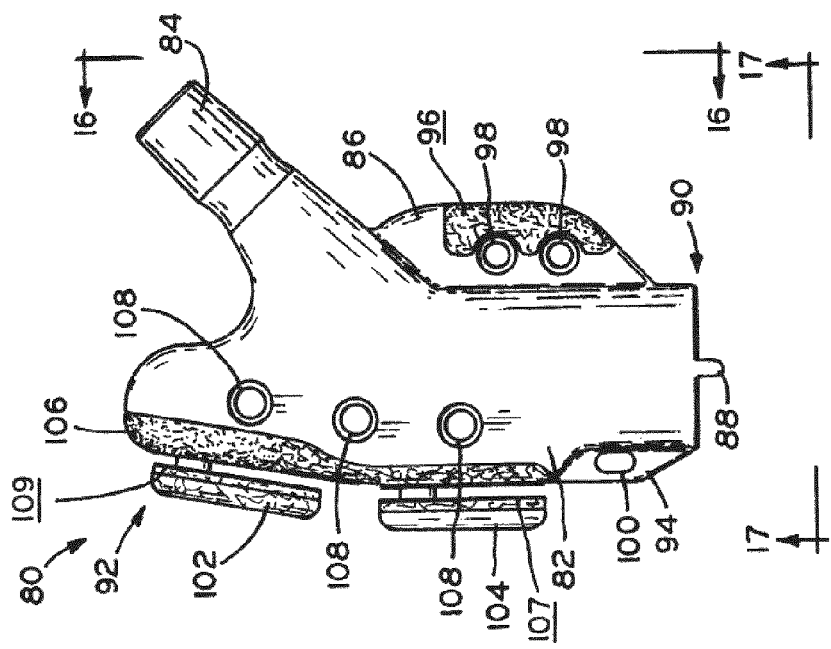
FIG_15

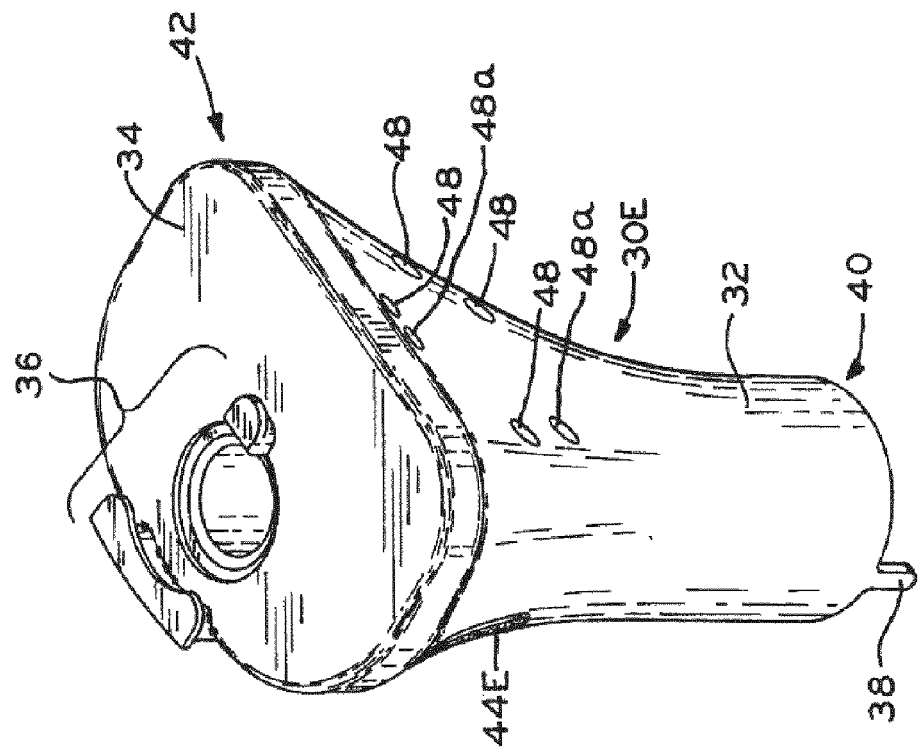
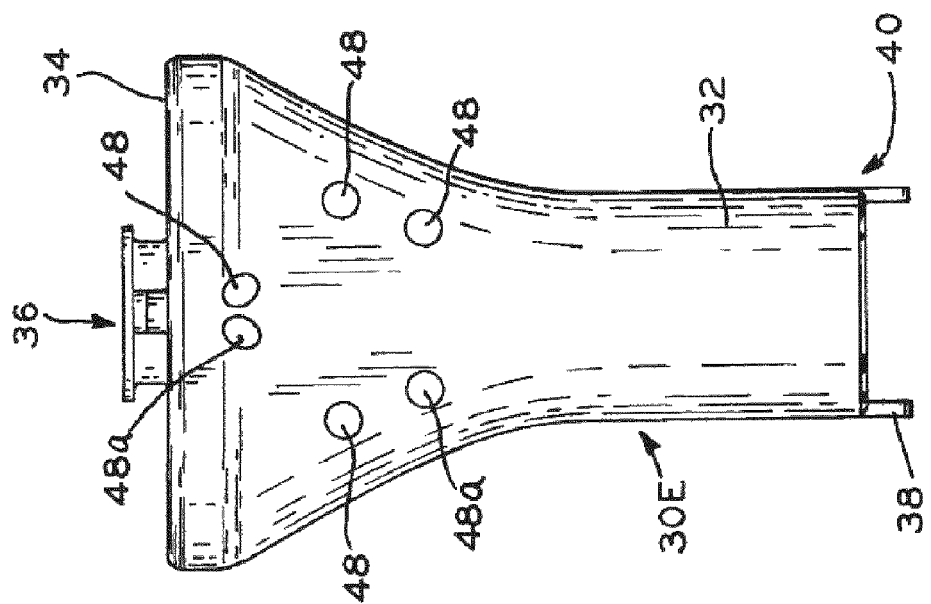

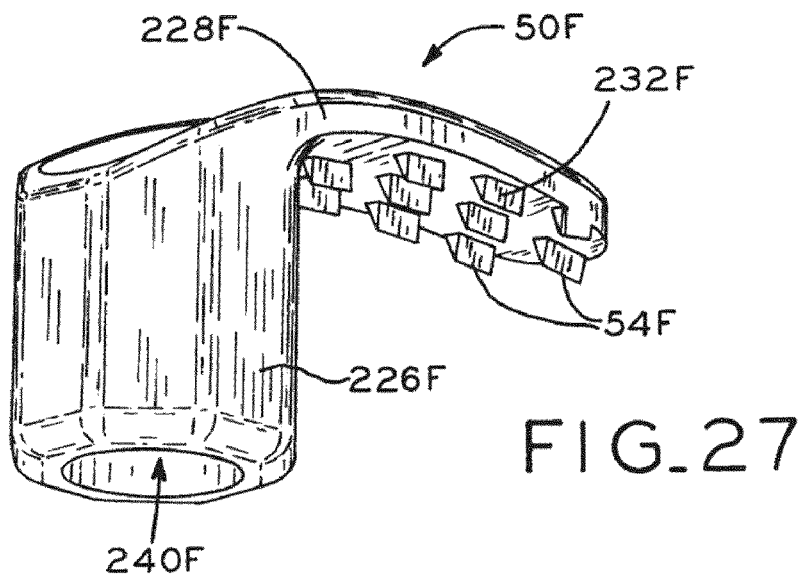
FIG_27
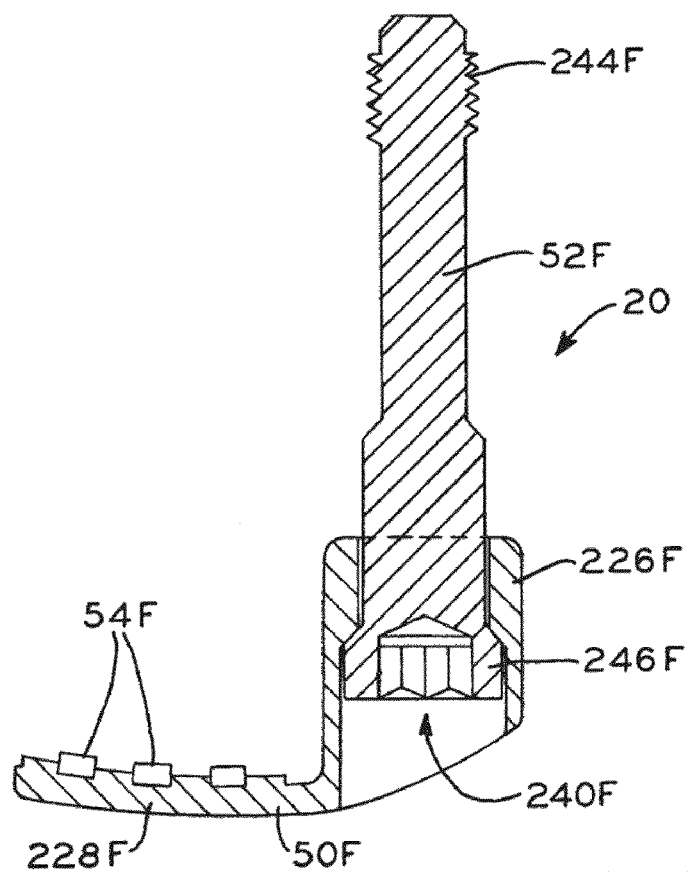
FIG_28

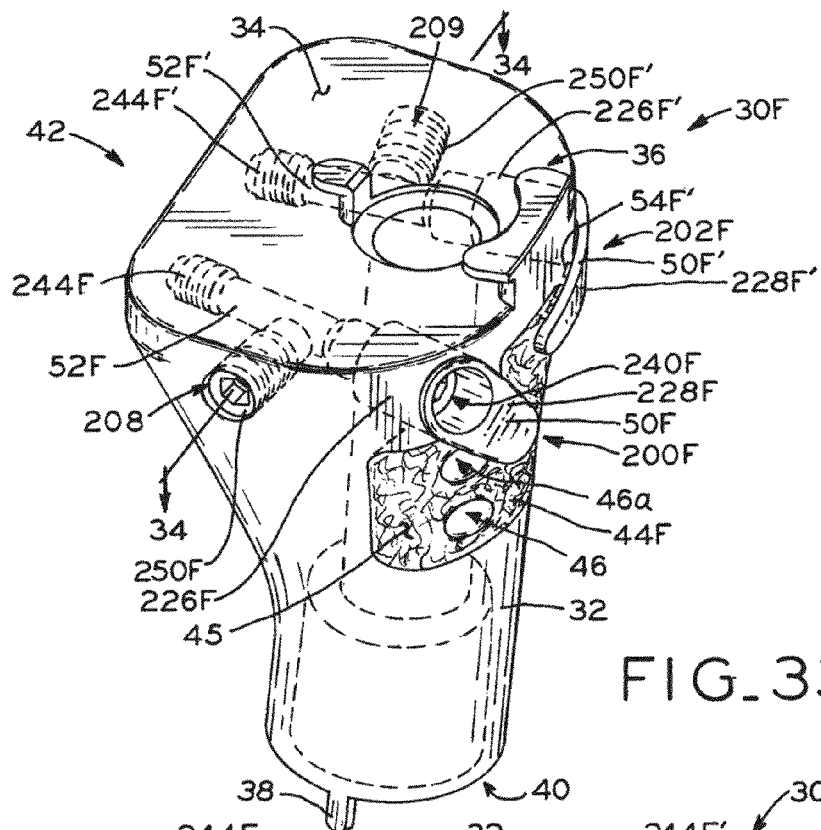
FIG_33
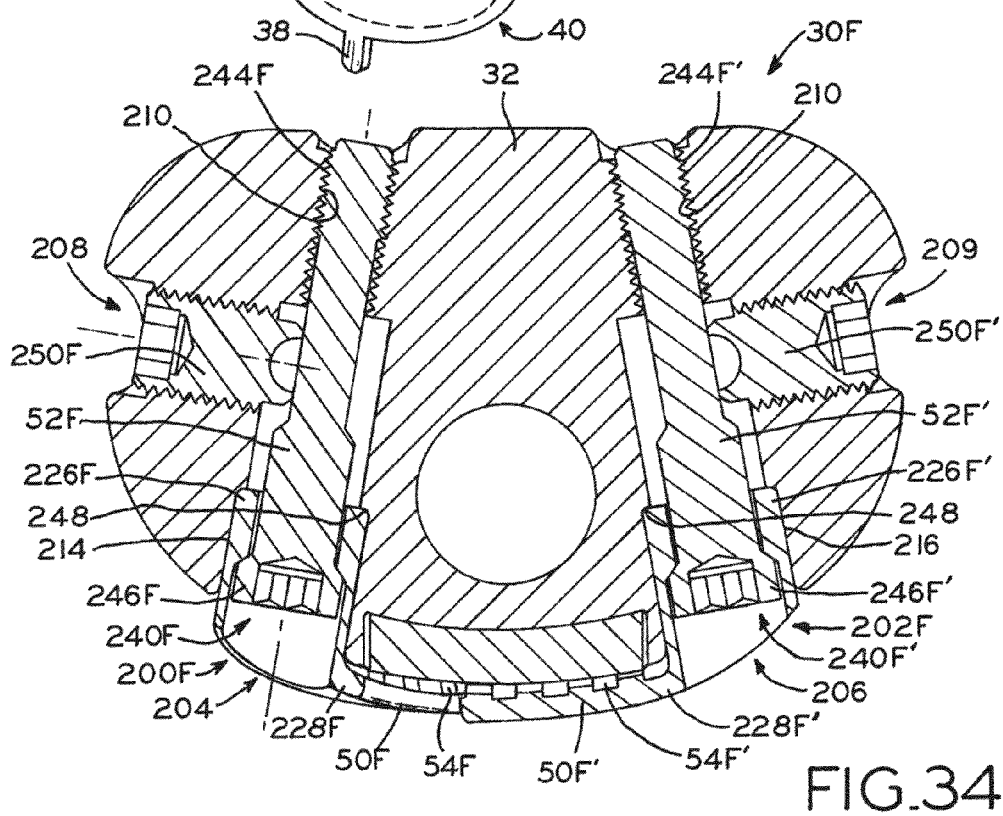
FIG.34

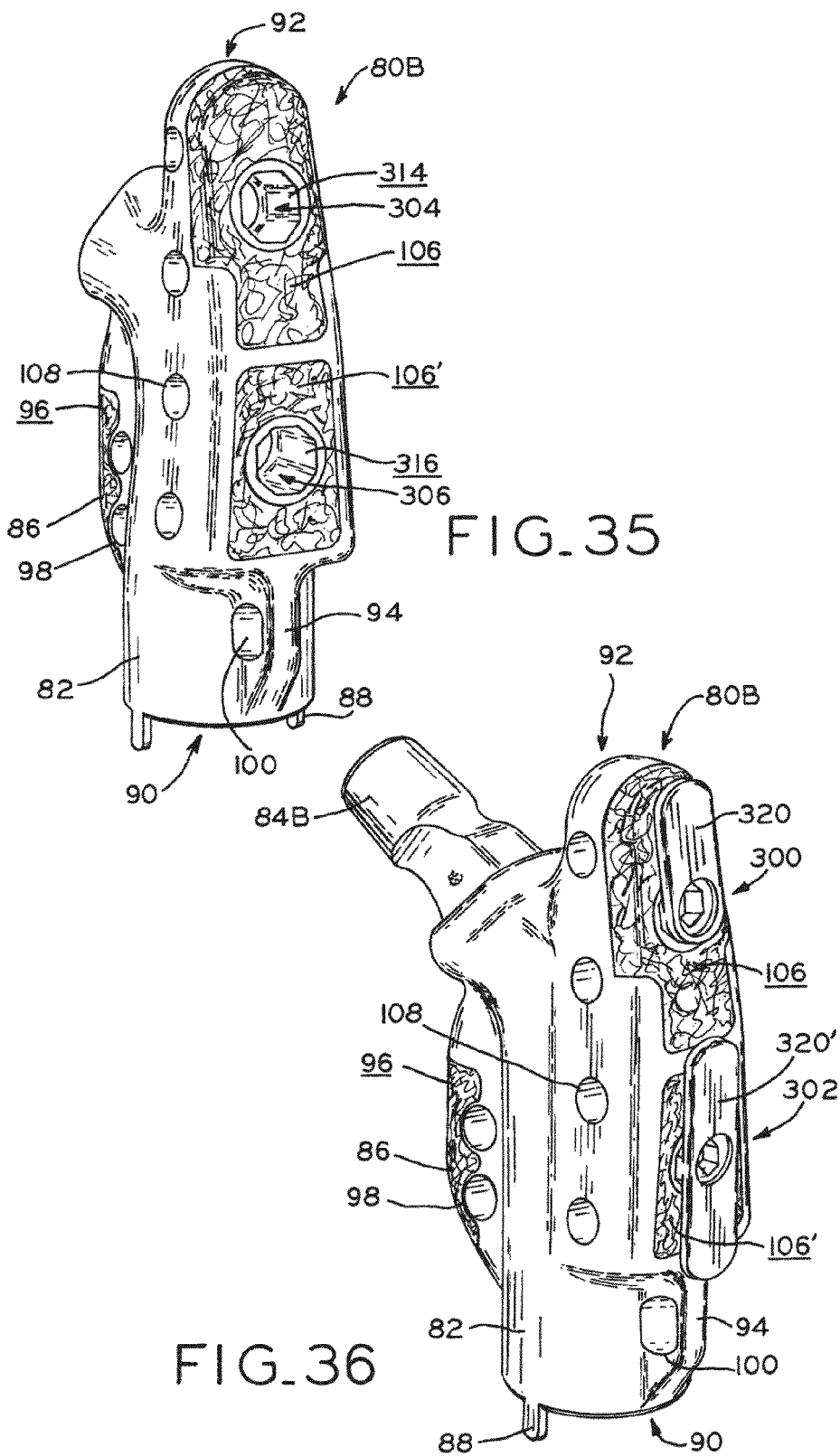

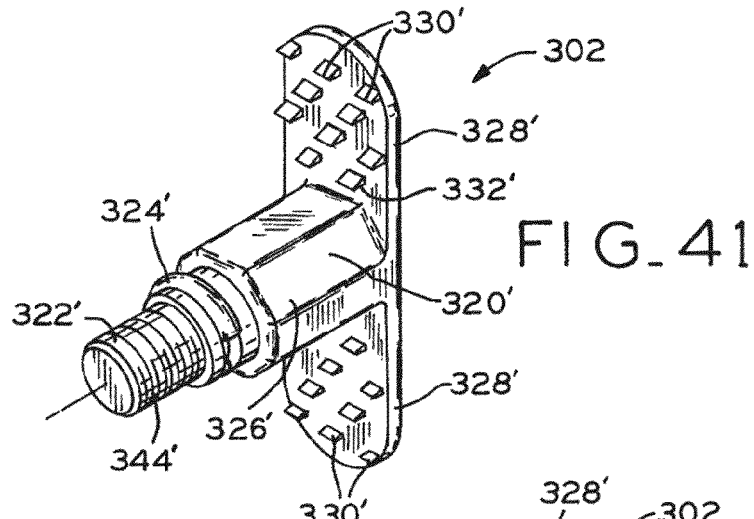
FIG_41
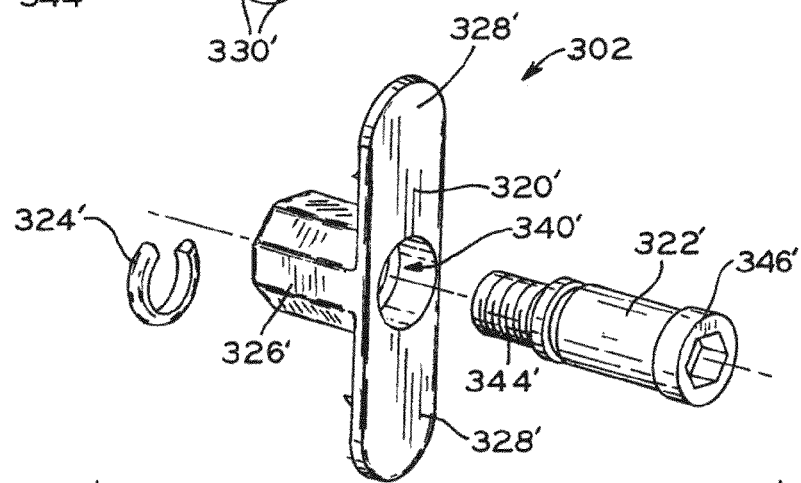
FIG_42
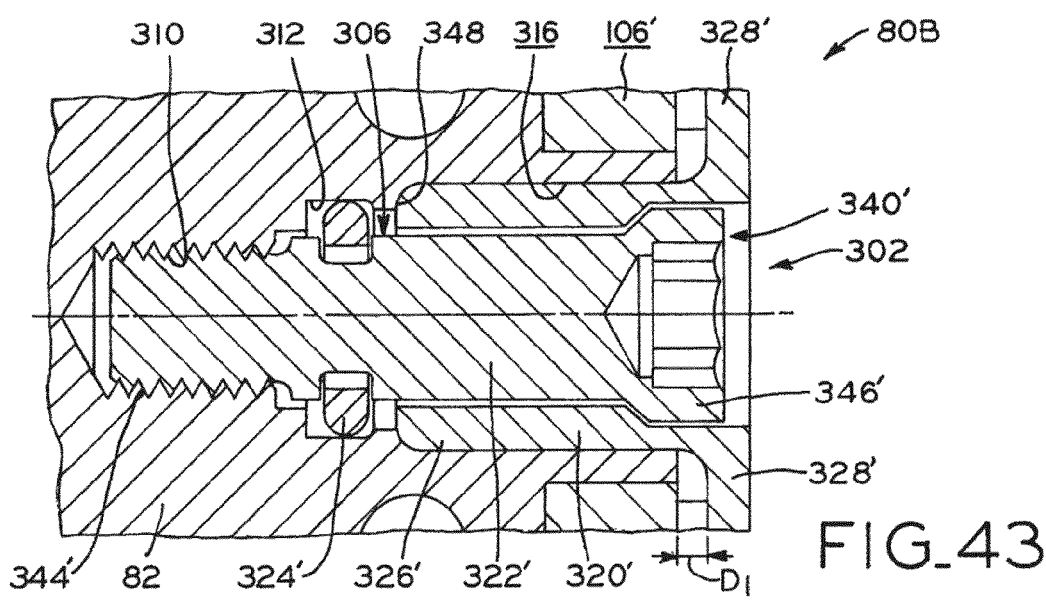
FIG_43

METHODS AND APPARATUSES FOR ATTACHING TISSUE TO ORTHOPAEDIC IMPLANTS

CROSS-REFERENCE TO RELATED APPLICATIONS

This application claims the benefit of U.S. Provisional Patent Application Ser. No. 60/916,414, entitled METHODS AND APPARATUSES FOR ATTACHING SOFT TISSUE TO ORTHOPAEDIC IMPLANTS, filed on May 7, 2007, and U.S. patent application Ser. No. 12/115,763, entitled METHODS AND APPARATUSES FOR ATTACHING SOFT TISSUE TO ORTHOPAEDIC IMPLANTS, filed on May 6, 2008, the entire disclosures of which are expressly incorporated by reference herein.

BACKGROUND

1. Field of the Disclosure

The present disclosure relates to methods and apparatuses for attaching tissue to orthopaedic implants. More particularly, the present disclosure relates to methods and apparatuses for attaching tissue to a proximal tibial implant and a proximal femoral implant.

2. Description of the Related Art

Orthopaedic implants are commonly used to replace at least a portion of a patient's joint to restore the use of the joint or to increase the use of the joint. For example, orthopaedic implants may be used to restore the patient's joint following deterioration due to aging or illness or following traumatic injury.

SUMMARY

The present disclosure provides methods and apparatuses for attaching tissue structures to orthopaedic implants. The tissue structures may include soft tissue structures, such as muscles, ligaments, capsules, and tendons. The tissue structures may also include bone, including bone that retains a natural connection to muscles, ligaments, capsules, or tendons. In one exemplary embodiment, the methods and apparatuses are used to attach a tissue structure to a proximal tibial implant. In another exemplary embodiment, the methods and apparatuses are used to attach a tissue structure to a proximal femoral implant.

According to an exemplary embodiment of the present invention, a segmental tibial orthopaedic implant configured for attachment to a tissue structure is provided. The segmental tibial orthopaedic implant includes a body and at least one washer. The body includes an anterior surface, a posterior surface, a lateral surface, a medial surface, a proximal end, and a distal end, the proximal end of the body including a bearing surface configured to support articulation with a distal femoral component, and the anterior surface of the body including a porous material. The at least one washer includes a clamping surface, the at least one washer rotatably coupled to the body with the clamping surface facing the anterior surface of the body, wherein the at least one washer is configured to clamp the tissue structure between the clamping surface and the anterior surface of the body.

According to another exemplary embodiment of the present invention, a segmental tibial orthopaedic implant configured for attachment to a tissue structure is provided. The segmental tibial orthopaedic implant includes a body, a medial washer, and a lateral washer. The body includes an anterior surface, a posterior surface, a lateral surface, a medial surface, a proximal end, and a distal end, the proximal end of the body including a bearing surface configured to support articulation with a distal femoral component. The medial washer is coupled to the body, the medial washer configured to clamp a medial tissue structure against the anterior surface of the body. The lateral washer is coupled to the body in spaced relation to the medial washer, the lateral washer configured to clamp a lateral tissue structure against the anterior surface of the body.

According to yet another exemplary embodiment of the present invention, a segmental femoral orthopaedic implant configured for attachment to a tissue structure is provided. The segmental femoral orthopaedic implant includes a body, a neck, and a protrusion. The body includes an anterior surface, a posterior surface, a lateral surface, a medial surface, a proximal end, and a distal end, the lateral surface of the body including a porous material. The neck extends medially from the body, the neck configured to support a head for articulation with an acetabular component. The protrusion projects medially from the body beneath the neck, the protrusion defining at least one suture throughbore.

According to yet another exemplary embodiment of the present invention, a method is provided for attaching a tissue structure to a segmental femoral orthopaedic implant. The method includes the steps of providing the segmental femoral orthopaedic implant comprising a body, a neck that extends from the body, and a protrusion that projects from the body beneath the neck, the protrusion defining at least one suture throughbore; implanting the segmental femoral orthopaedic implant in a patient such that the neck and the protrusion extend medially from the body; and securing the tissue structure to the protrusion.

According to yet another exemplary embodiment of the present invention, a segmental femoral orthopaedic implant configured for attachment to a tissue structure is provided. The segmental femoral orthopaedic implant includes a body, a neck, a proximal washer, and a distal washer. The body includes an anterior surface, a posterior surface, a lateral surface, a medial surface, a proximal end, and a distal end, the lateral surface of the body including a porous material. The neck extends medially from the body, the neck configured to support a head for articulation with an acetabular component. The proximal washer is coupled to the body, the proximal washer configured to resist movement of a proximal tissue structure in a first direction. The distal washer is coupled to the body distally of the proximal washer, the distal washer configured to resist movement of a distal tissue structure in a second direction that differs from the first direction.

According to still yet another exemplary embodiment of the present invention, an orthopaedic implant configured for attachment to a tissue structure is provided. The orthopaedic implant includes a body and at least one washer rotatably coupled to the body. The body includes an anterior surface, a posterior surface, a lateral surface, a medial surface, a proximal end, and a distal end, the proximal end of the body configured for articulation with an adjacent anatomical structure, and at least one of the anterior, posterior, lateral, and medial surfaces of the body including a porous material. The at least one washer is configured to clamp the tissue structure against the porous material of the body, the at least one washer maintaining a fixed axial spacing from the body as the at least one washer is rotated relative to the body from a first rotational position to a second rotational position.

According to still yet another exemplary embodiment of the present invention, an orthopaedic implant configured for attachment to a tissue structure is provided. The orthopaedic implant includes a body, a first washer, a second washer, and a fastener. The body includes an anterior surface, a posterior surface, a lateral surface, a medial surface, a proximal end, and a distal end, the proximal end of the body configured for articulation with an adjacent anatomical structure, the body defining a bore. The first washer includes a first body portion and a first engagement arm, the first body portion configured to extend into the bore of the implant, the first engagement arm separated a first distance from the body of the implant when the first body portion is received in the bore and configured to clamp the tissue structure against the body of the implant. The second washer includes a second body portion and a second engagement arm, the second body portion configured to extend into the same bore of the implant as the first body portion of the first washer, the second engagement arm separated a second distance from the body of the implant when the second body portion is received in the bore and configured to clamp the tissue structure against the body of the implant, the second distance exceeding the first distance. The fastener is configured to extend into the bore of the implant to couple either of the first and second washers to the body of implant.

According to still yet another exemplary embodiment of the present invention, a method is provided for attaching a tissue structure to an orthopaedic implant. The method includes the steps of: providing a body including an anterior surface, a posterior surface, a lateral surface, a medial surface, a proximal end, and a distal end, the proximal end of the body configured for articulation with an adjacent anatomical structure; providing a porous plate including at least one suture throughbore; securing the tissue structure to the plate; and after the securing step, coupling the plate to the body.

BRIEF DESCRIPTION OF THE DRAWINGS

The above-mentioned and other features of the disclosure, and the manner of attaining them, will become more apparent and will be better understood by reference to the following description of embodiments of the disclosure taken in conjunction with the accompanying drawings, wherein:

FIG. 3 is a side elevational view of the proximal tibial implant of FIG. 1;

FIG. 4 is an anterior elevational view of the proximal tibial implant of FIG. 1;

FIG. 5 is another side elevational view of the proximal tibial implant of FIG. 1;

FIG. 6 is an anterior elevational view of the proximal tibial implant of FIG. 1, further including a medial rotating fixation structure and a lateral rotating fixation structure, each having a washer and a fastener;

FIG. 7 is a cross-sectional view of the washer and the fastener of FIG. 6;

FIG. 8 is an alternative cross-sectional view of the washer and the fastener of FIG. 6;

FIG. 11 is a perspective view of a proximal tibial implant according to yet another exemplary embodiment of the present disclosure;

FIG. 12 is a cross-sectional view of the proximal tibial implant of FIG. 11, taken along line 12-12 of FIG. 11;

FIG. 15 is an anterior/posterior elevational view of the proximal femoral implant of FIG. 13;

FIG. 16 is a medial elevational view of the proximal femoral implant of FIG. 15, taken along line 16-16 of FIG. 15;

FIG. 17 is an inferior plan view of the proximal femoral implant of FIG. 15, taken along line 17-17 of FIG. 15;

FIG. 20 is a posterior elevational view of the proximal tibial implant of FIG. 18;

FIG. 21 is a perspective view of the proximal tibial implant of FIG. 18;

FIG. 27 is a perspective view of the washer of FIG. 26;

FIG. 28 is a cross-sectional view of the washer and the fastener of FIG. 26;

FIG. 33 is a perspective view of the proximal tibial implant of FIG. 26, further including a set screw;

FIG. 34 is a cross-sectional view of the proximal tibial implant of FIG. 33, taken along line 34-34 of FIG. 33;

FIG. 35 is a perspective view of a proximal femoral implant according to another exemplary embodiment of the present disclosure;

FIG. 36 is a perspective view of the proximal femoral implant of FIG. 35, further including a proximal rotating fixation structure and a distal rotating fixation structure;

FIG. 41 is a perspective view of the distal rotating fixation structure of FIG. 36;

FIG. 42 is an exploded perspective view of the distal rotating fixation structure of FIG. 36;

FIG. 43 is a partial cross-sectional view of the proximal femoral implant and the distal rotating fixation structure of FIG. 36;

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 1:
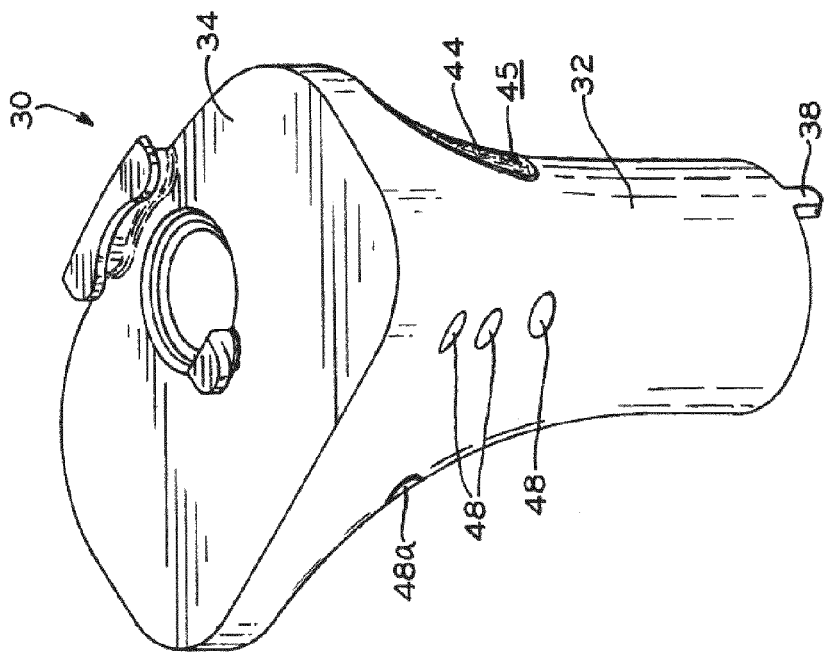
FIG. 1 is a perspective view of a proximal tibial implant according to an exemplary embodiment of the present disclosure.
Figure 2:
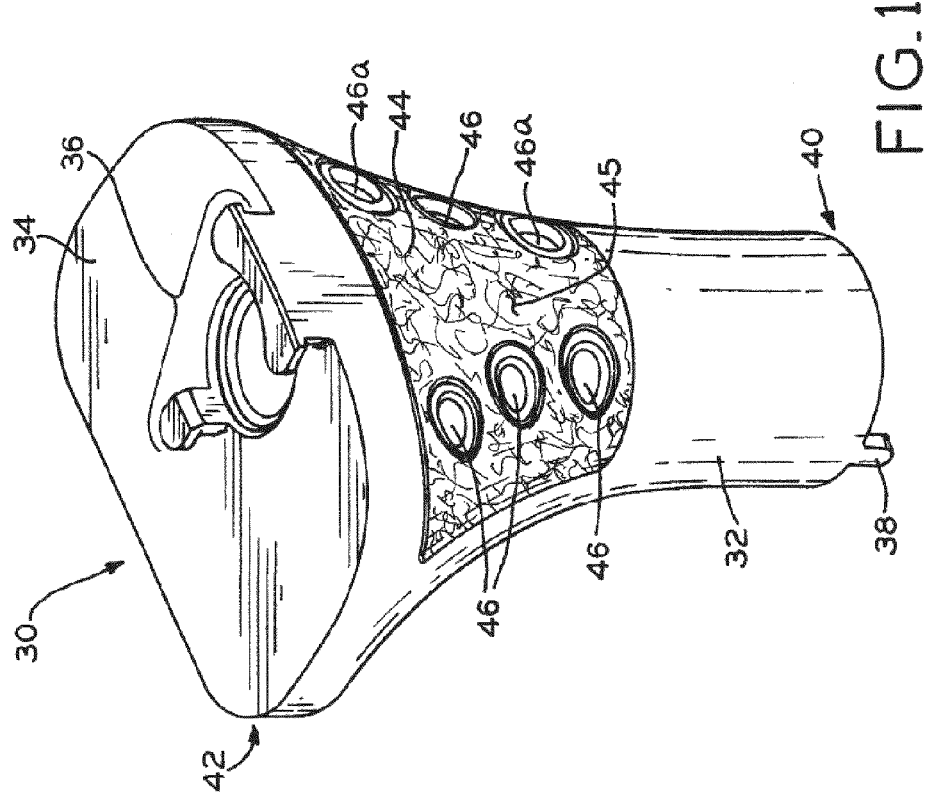
FIG. 2 is another perspective view of the proximal tibial implant of FIG. 1.

Referring to FIGS. 1-5, proximal tibial implant 30 is shown and may be used to restore mechanical and biological fixation of tissue structures associated with a knee joint of a patient to enhance the stability of the knee joint, to restore knee joint function, and to enhance knee joint kinematics. The tissue structures may include soft tissue structures, such as muscles, ligaments, capsules, and tendons. The tissue structures may also include bone, including bone that retains a natural connection to muscles, ligaments, capsules, or tendons. Typically, proximal tibial implant 30 may be used in a patient requiring complete metaphyseal removal of the proximal tibia. Proximal tibial implant 30 of FIG. 1 includes body 32 having proximal end 42 and distal end 40, femoral bearing plate or surface 34, and mating structure 36. Body 32 also includes an anterior surface, a posterior surface opposite the anterior surface, a lateral surface, and a medial surface opposite the lateral surface.

Body 32 may be formed from relatively light-weight material, such as titanium, a cobalt chromium alloy, or another suitable biocompatible material, for example, thereby making it easier for the patient to lift and extend the knee joint, particularly in procedures which require extensive removal of muscle proximate the knee joint. In one embodiment, bearing surface 34 may be formed as a modular component of proximal tibial implant 30 to provide more interoperative options. In an exemplary embodiment, bearing surface 34 is formed of a wear-resistant material to minimize debris from articulation with an adjacent anatomical component of the knee joint, such as a distal femoral component (not shown). Mating structure 36 may be formed complementary to a meniscal component (not shown) of the knee joint to provide either a mobile or a non-mobile bearing connection between proximal tibial implant 30 and the meniscal component.

As shown in FIG. 1, proximal tibial implant 30 also includes rotational adjustment tabs 38 at distal end 40 of proximal tibial implant 30 to allow for in vivo rotational adjustment of proximal tibial implant 30 relative to another implant or to the remaining structure of the tibia. Rotational adjustment tabs 38 may generally extend distally from body 32 along a lateral and/or a medial side of proximal tibial implant 30. A plurality of tabs 38 may be utilized or a single tab 38 may be utilized.

Proximal tibial implant 30 further includes tissue attachment plate 44. In an exemplary embodiment, attachment plate 44 is positioned on at least an anterior surface of proximal tibial implant 30. Attachment plate 44 may be integrally formed with proximal tibial implant 30. Alternatively, attachment plate 44 may be formed as a modular component of proximal tibial implant 30. The modular attachment plate 44 may be positioned in a recess (not shown) on the anterior surface of proximal tibial implant 30 and fastened to body 32. Attachment plate 44 may generally have a relatively thin anterior to posterior thickness, e.g., as low as approximately 1 mm to as high as approximately 5 mm, such as to define a relatively slim profile. In an embodiment, attachment plate 44 does not protrude from proximal tibial implant 30 to avoid potentially interfering with other anatomical structures. For example, the anterior surface of attachment plate 44 may sit substantially flush with the remainder of the anterior surface of proximal tibial implant 30. Alternatively, in another embodiment, attachment plate 44 may sit proud of proximal tibial implant 30 to enhance the attachment to tissue structures. For example, the anterior surface of attachment plate 44 may extend 0.5 mm, 1 mm, or more, beyond proximal tibial implant 30.

Attachment plate 44 provides a direct connection between a tissue structure and proximal tibial implant 30. For example, a patellar tendon, which joins a lower edge of a patella (not shown) of the knee joint with a tibial tubercle of a tibia, may be mechanically fixed directly to attachment plate 44 of proximal tibial implant 30. Also, the patellar tendon may be biologically fixed via ingrowth into attachment plate 44 of proximal tibial implant 30. Such fixation of the patellar tendon to proximal tibial implant 30 enhances usability of the knee joint. For example, when a patient jumps into the air or allows the tibia to hang without any support, the fixation of the patellar tendon to proximal tibial implant 30 prevents dislocation of the components of the prosthetic knee joint and facilitates normal functioning of the prosthetic knee joint after the jump or once the tibia is again supported. In one example, a rotating hinged knee includes a distal femoral component with a post extending through a meniscal component and into proximal tibial implant 30. During a jump or when the tibia is unsupported, the patellar tendon effectively prevents the post from extending too far from proximal tibial implant 30 and ensures that the post returns to proper engagement with proximal tibial implant 30 once normal functioning is resumed.

As described further below, attachment plate 44 includes at least one porous surface 45, such as a surface to facilitate ingrowth of tissue structures. In one embodiment, porous surface 45 may be formed of a material having a cellular structure which resembles bone and approximates the physical and mechanical properties of bone, thereby enabling rapid and extensive tissue infiltration and strong attachment of tissue structures thereto. For example, the material may be a highly porous biomaterial having a porosity as low as 55, 65, or 75 percent and as high as 80, 85, or 90 percent. An example of such a material is produced using Trabecular Metal™ technology that is generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861, the disclosure of which is expressly incorporated herein by reference. In addition to tantalum, other metals such as niobium or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone and/or soft tissue through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone. The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization. Such porous material also facilitates ingrowth of soft tissue for enhanced attachment of soft tissue structures to proximal tibial implant 30. For example, fibers and struts which extend from porous surface 45 are generally rough which facilitates holding a soft tissue structure in such a manner that damage and disengagement of the soft tissue structure is discouraged. The porous material may have a generally corrugated surface to further facilitate biological fixation of soft tissue structures thereto.

According to an exemplary embodiment of the present invention, porous surface 45 of attachment plate 44 may be impregnated with and/or coated with biologically active agents. Suitable biologically active agents include, for example, antibiotics, to reduce the chances of infection and to promote healing, and growth factors, to promote ingrowth into porous surface 45 of attachment plate 44.

As shown in FIGS. 3-5, proximal tibial implant 30 further includes fastener or suture apertures 46 in the anterior surface of body 32 aligned with corresponding throughbores 48 that extend posteriorly through body 32 of proximal tibial implant 30. Throughbores 48 generally extend straight through proximal tibial implant 30 from the anterior surface to the posterior surface. Also, body 32 may include apertures 46a which are generally skewed through body 32. Apertures 46a may include corresponding throughbores 48a that form a curved path through body 32, as opposed to a straight path through body 32 as formed by throughbores 48. Advantageously, apertures 46a and their respective curved throughbores 48a may accommodate curved suture needles. In addition, apertures 46, 46a, may be counterbored, as shown, for example, in FIG. 3. Counterbored apertures 46, 46a, increase the space available to insert a suture needle into the corresponding throughbores 48, 48a, without having to widen throughbores 48, 48a, entirely across the depth of body 32, which could reduce the strength of body 32. Like curved throughbores 48a, counterbored apertures 46, 46a, may accommodate curved suture needles in the corresponding throughbores 48, 48a. Apertures 46, 46a, may have a generally rounded shape to facilitate prevention of suture or fastener breakage during an operation.

In operation, a surgeon may attach a tissue structure, such as a muscle, a ligament, a capsule, a tendon, and/or bone, for example, to proximal tibial implant 30. First, the surgeon positions the tissue structure in contact with attachment plate 44. At least one suture is then threaded through apertures 46, 46a, and the corresponding throughbores 48, 48a, to maintain contact between the tissue structure and attachment plate 44. In contrast to sutures, a surgeon may also use surgical tape or surgical cables, for example. The surgeon may select any or all apertures 46, 46a, and throughbores 48, 48a, to at least temporarily secure the tissue structure to attachment plate 44 of proximal tibial implant 30. In one embodiment, the sutures may be biodegradable after a period of time in which the tissue structure is permanently attached to proximal tibial implant 30 via ingrowth of the tissue structure into porous surface 45 of attachment plate 44. The close proximity of apertures 46, 46a, to attachment plate 44 facilitates more direct contact between the tissue structure and attachment plate 44.

Referring next to FIGS. 6-8, an alternative embodiment proximal tibial implant 30A is shown and is substantially identical to proximal tibial implant 30, described above with reference to FIGS. 1-5, except as described below. Proximal tibial implant 30A includes body 32, bearing surface 34, mating structure 36, rotational adjustment tabs 38, distal end 40, and proximal end 42. Proximal tibial implant 30A also includes attachment plate 44A which is similar to attachment plate 44, described above with reference to FIGS. 1-5, except as described below. For example, attachment plate 44A on the anterior surface of proximal tibial implant 30A includes porous surface 45 to facilitate ingrowth of a tissue structure.

Proximal tibial implant 30A also includes medial fixation structure 200 and lateral fixation structure 202. Medial fixation structure 200 includes washer 50 and fastener 52, and lateral fixation structure 202 includes washer 50' and fastener 52'. Washers 50, 50', may be attached atop attachment plate 44A by inserting fasteners 52, 52', through any apertures 46 provided in body 32. It is within the scope of the present invention that washers 50, 50', may be labeled to ensure that washer 50 is inserted into body 32 medially of washer 50'. Also, each washer 50, 50', and/or fastener 52, 52', may be sized or shaped to fit into a particular aperture 46 to ensure that washer 50 is inserted into body 32 medially of washer 50'. Washers 50, 50', are rotatably attached to attachment plate 44A such that washers 50, 50', are rotatable from a first rotational position, shown in phantom in FIG. 6, in which a tissue structure is not engaged with washers 50, 50', to a second rotational position, shown in solid lines in FIG. 6, in which a tissue structure may be securely clamped against attachment plate 44A of proximal tibial implant 30A with washers 50, 50'. In one embodiment, as shown in FIG. 7, washer 50 includes a plurality of teeth 54 to further facilitate holding engagement of the tissue structure against attachment plate 44A with washer 50. In another embodiment, as shown in FIG. 8, washer 50 includes a porous material similar to porous surface 45 described above to facilitate ingrowth of the tissue structure into both washer 50 and attachment plate 44A, thereby facilitating a secure hold on the tissue structure.

In operation, a surgeon may attach tissue structures to proximal tibial implant 30A. The tissue structures may include soft tissue structures, such as muscles, ligaments, capsules, and tendons. The tissue structures may also include bone, including bone that retains a natural connection to muscles, ligaments, capsules, or tendons. First, the surgeon positions the tissue structure in contact with attachment plate 44A. At least one optional washer 50, 50', may then be rotated from the first rotational position into the second rotational position, as shown in FIG. 6, to clamp and mechanically fix the tissue structure to attachment plate 44A beneath washers 50, 50'. Each washer 50, 50', may include a locking mechanism to lock washers 50, 50', in the clamped, second rotational position. In an exemplary procedure, a surgeon pulls or otherwise manipulates a tissue structure, such as a portion of a calf muscle or the patellar tendon, for example, in close proximity to attachment plate 44A, and then uses washers 50, 50', to clamp the tissue structure against porous surface 45 of attachment plate 44A, such that the tissue structure is mechanically fixed to proximal tibial implant 30A beneath washers 50, 50'. Washers 50, 50', may be positioned to pull the tissue structure from a medial, lateral, proximal, and/or distal side of proximal tibial implant 30A.

To further maintain contact between the tissue structure and attachment plate 44A, the surgeon may thread at least one suture through apertures 46, 46a, and the corresponding throughbores 48, 48a, to create a "sling" around proximal tibial implant 30A. The surgeon may select any or all apertures 46, 46a, and the corresponding throughbores 48, 48a, to secure the tissue structure to proximal tibial implant 30A. In one embodiment, the sutures may be biodegradable after a period of time in which the tissue structure is permanently attached to proximal tibial implant 30A via ingrowth of the tissue structure into porous surface 45 of attachment plate 44A. The close proximity of apertures 46, 46a, to attachment plate 44A facilitates more direct contact between the tissue structure and attachment plate 44A and encourages ingrowth of the tissue structure into porous surface 45 of attachment plate 44A. According to an exemplary embodiment of the present disclosure, sutures are used in combination with washers 50, 50', to biologically and mechanically fix the tissue structure to proximal tibial implant 30A.

Figure 9:
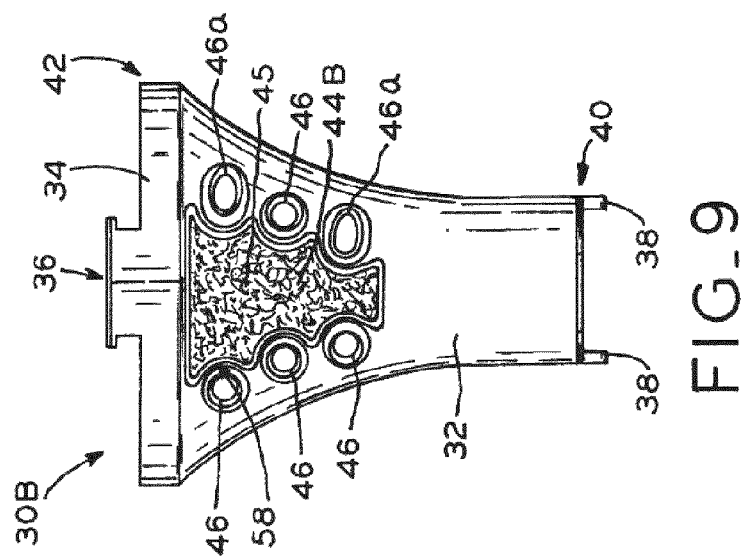
FIG. 9 is an anterior elevational view of a proximal tibial implant according to another exemplary embodiment of the present disclosure.

Referring next to FIG. 9, another embodiment proximal tibial implant 30B is shown and may be substantially identical to proximal tibial implant 30, described above with reference to FIGS. 1-5, or proximal tibial implant 30A, described above with reference to FIGS. 6-8, except as described below. Proximal tibial implant 30B includes body 32, bearing surface 34, mating structure 36, rotational adjustment tabs 38, distal end 40, and proximal end 42. Proximal tibial implant 30B also includes attachment plate 44B which is similar to attachment plate 44, described above with reference to FIGS. 1-5, or attachment plate 44A, described above with reference to FIGS. 6-8, except as described below. For example, attachment plate 44B on the anterior surface of proximal tibial implant 30B includes porous surface 45 to facilitate ingrowth of a tissue structure.

As shown in FIG. 9, apertures 46, 46a, in body 32 are at least partially offset from porous surface 45 of attachment plate 44B, as opposed to extending through attachment plate 44B and being surrounded by porous surface 45, as shown in FIG. 1. In this embodiment, contact between the fragile sutures that extend through apertures 46, 46a, and the rough, uneven porous surface 45, may be reduced and/or eliminated, thereby minimizing the risk that the sutures will weaken or tear. Attachment plate 44B may include contours 58 which substantially mimic the shape of apertures 46, 46a, on one side, extending porous surface 45 adjacent to and in close proximity to each aperture 46, 46a, on one side. Contours 58 encourage contact between the tissue structure and porous surface 45 on one side of apertures 46, 46a, while still reducing and/or eliminating contact between the fragile sutures and porous surface 45 on the other side of apertures 46, 46a.

In operation, a surgeon may attach a tissue structure to proximal tibial implant 30B. First, the surgeon positions the tissue structure in contact with attachment plate 44B. At least one suture is then threaded through apertures 46, 46a, and the corresponding throughbores 48, 48a, to maintain contact between the tissue structure and attachment plate 44B. The surgeon may select any or all apertures 46, 46a, and the corresponding throughbores 48, 48a, to secure the tissue structure to proximal tibial implant 30B. In one embodiment, the sutures may be biodegradable after a period of time in which the tissue structure is permanently attached to proximal tibial implant 30B via ingrowth of the tissue structure into porous surface 45 of attachment plate 44B. The close proximity of apertures 46, 46a, to attachment plate 44B facilitates more direct contact between the tissue structure and attachment plate 44B. At the same time, providing a non-porous area around at least a portion of each aperture 46, 46a, may reduce contact between the sutures and the rough, uneven porous surface 45, which could tear the sutures.

Figure 10:
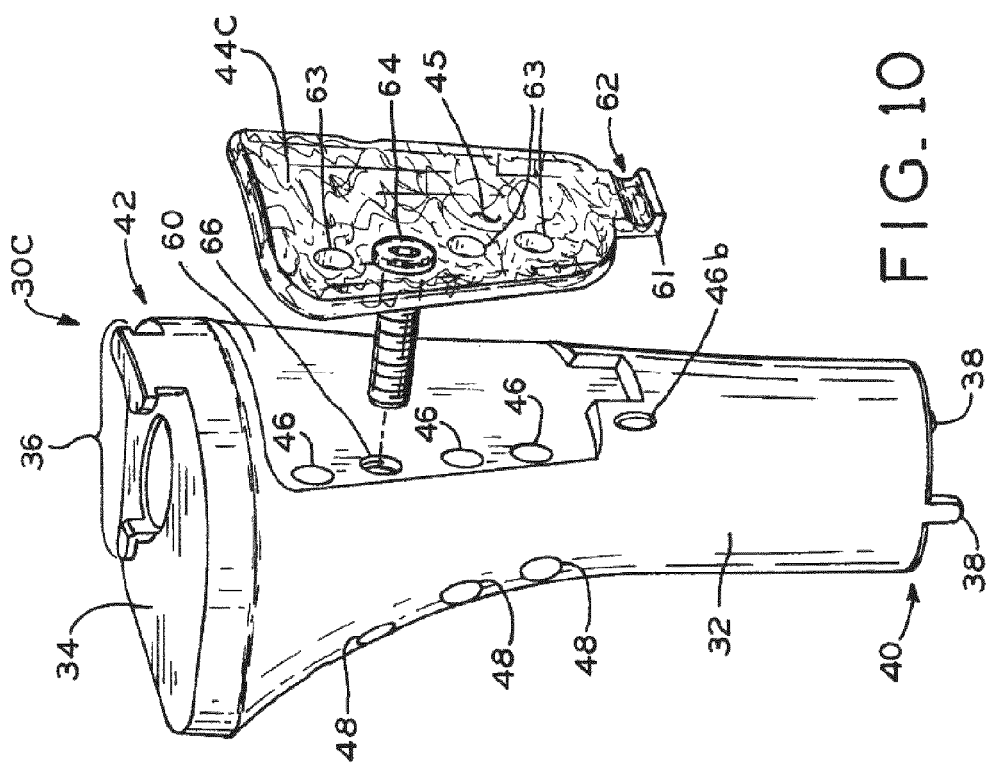
FIG. 10 is an exploded perspective view of a proximal tibial implant according to yet another exemplary embodiment of the present disclosure.

Referring next to FIG. 10, yet another embodiment proximal tibial implant 30C is shown and may be substantially identical to proximal tibial implant 30, described above with reference to FIGS. 1-5, proximal tibial implant 30A, described above with reference to FIGS. 6-8, or proximal tibial implant 30B, described above with reference to FIG. 9, except as described below. Proximal tibial implant 30C includes body 32, bearing surface 34, mating structure 36, rotational adjustment tabs 38, distal end 40, and proximal end 42. Proximal tibial implant 30C also includes attachment plate 44C which may be similar to attachment plate 44, described above with reference to FIGS. 1-5, attachment plate 44A, described above with reference to FIGS. 6-8, or attachment plate 44B, described above with reference to FIG. 9, except as described below. For example, attachment plate 44C on the anterior surface of proximal tibial implant 30C includes porous surface 45 to facilitate ingrowth of a tissue structure.

As shown in FIG. 10, attachment plate 44C is a modular component, which may be attached to body 32 via fastener 64 inserted through attachment plate 44C and into a corresponding aperture 66 in body 32, for example. Fastener 64 may be a screw, bolt, anchor mechanism, a mechanism which expands once inserted into body 32, or any other suitable fastening mechanism. Body 32 includes recess 60 formed in an anterior surface of body 32 that is sized and configured to accept attachment plate 44C in a close-fitting engagement. Recess 60 in body 32 also provides clearance for extension 61 of attachment plate 44C which includes groove 62. In one embodiment, attachment plate 44C may include a smooth posterior surface to facilitate the close-fitting engagement with recess 60. In another embodiment, the posterior surface of attachment plate 44C and/or the surface of recess 60 may include a porous surface substantially identical to porous surface 45 described above.

In operation, a surgeon may attach a tissue structure to proximal tibial implant 30C with attachment plate 44C already attached to body 32. First, the surgeon positions the tissue structure in contact with attachment plate 44C. At least one suture is then threaded through apertures 46, 46a, and the corresponding throughbores 48, 48a, to maintain contact between the tissue structure and attachment plate 44C. The surgeon may select any or all apertures 46, 46a, and the corresponding throughbores 48, 48a, to secure the tissue structure to proximal tibial implant 30C. Furthermore, the surgeon may thread at least one suture through groove 62 and around extension 61 of attachment plate 44C and through distal aperture 46b in body 32 to further facilitate mechanical fixation and stabilization of modular attachment plate 44C to body 32 and/or the tissue structure to attachment plate 44C. In one embodiment, the sutures may be biodegradable after a period of time in which the tissue structure is permanently attached to proximal tibial implant 30C via ingrowth of the tissue structure into porous surface 45 of attachment plate 44C. The close proximity of apertures 46, 46a, 46b, to attachment plate 44C facilitates more direct contact between the tissue structure and attachment plate 44C, thereby enhancing the ingrowth of the tissue structure into porous surface 45 of attachment plate 44C.

Alternatively, in certain embodiments, the surgeon may first attach the tissue structure to the modular attachment plate 44C and then secure attachment plate 44C to body 32, thereby providing potential for tensioning the tissue structure prior to securement of attachment plate 44C to body 32. For example, the surgeon may tie the tissue structure onto attachment plate 44C by tying a suture through apertures 63 and/or along groove 62. To further maintain contact between the tissue structure and proximal tibial implant 30C, the surgeon may position the tissue structure between the modular attachment plate 44C and body 32 and then clamp attachment plate 44C onto body 32 using fastener 64. Providing a porous surface on the posterior surface of attachment plate 44C and/or the surface of recess 60 would further facilitate ingrowth of the tissue structure into proximal tibial implant 30C. In this embodiment, the anterior surface of attachment plate 44C may be non-porous to avoid interfering with surrounding tissue, including skin. In one embodiment, attachment plate 44C is formed of a material which allows tissue and blood vessels to grow through the plate. In this manner, attachment plate 44C may secure a soft tissue structure, such as the patellar tendon, to proximal tibial implant 30C and then a muscle, such as a calf muscle, may be wrapped over the anterior surface of attachment plate 44C to facilitate blood flow through attachment plate 44C, thereby reducing the potential of subcutaneous irritation and necrosis of the soft tissue structures.

Referring next to FIGS. 11-12, yet another embodiment proximal tibial implant 30D is shown and may be substantially identical to proximal tibial implant 30, described above with reference to FIGS. 1-5, proximal tibial implant 30A, described above with reference to FIGS. 6-8, proximal tibial implant 30B, described above with reference to FIG. 9, or proximal tibial implant 30C, described above with reference to FIG. 10, except as described below. Proximal tibial implant 30D includes body 32, bearing surface 34, mating structure 36, rotational adjustment tabs 38, distal end 40, and proximal end 42. Proximal tibial implant 30D also includes attachment plate 44D which may be similar to attachment plate 44, described above with reference to FIGS. 1-5, attachment plate 44A, described above with reference to FIGS. 6-8, attachment plate 44B, described above with reference to FIG. 9, or attachment plate 44C, described above with reference to FIG. 10, except as described below. For example, attachment plate 44C on the anterior surface of proximal tibial implant 30D includes porous surface 45 to facilitate ingrowth of a tissue structure. Attachment plate 44D may be a modular component and attached to body 32 via suitable fasteners (not shown), an adhesive material, an interference fit, or, alternatively, attachment plate 44D may be integrally formed with body 32.

As shown in FIG. 12, body 32 includes apertures 46, corresponding throughbores 48, posterior recesses 68, and anterior recesses 70. It is within the scope of the present invention that recesses 68, 70, may be formed on one or both medial and lateral sides of body 32. Posterior recesses 68 may be formed toward the posterior side of body 32 but maintain proximity to the anterior side of body 32. Anterior recesses 70 may be formed on the anterior side of body 32 adjacent to attachment plate 44D. The corresponding throughbore 48 of each aperture 46 extends width W from anterior recess 70 to a corresponding posterior recess 68.

In operation, a surgeon may attach a tissue structure to proximal tibial implant 30D. First, the surgeon positions the tissue structure in contact with attachment plate 44D. At least one suture is then threaded through apertures 46 and the corresponding throughbores 48 to maintain contact between the tissue structure and attachment plate 44D. The surgeon may select any or all apertures 46 and the corresponding throughbores 48 to secure the tissue structure to proximal tibial implant 30D. In one embodiment, the sutures may be biodegradable after a period of time in which the tissue structure is permanently attached to proximal tibial implant 30D via ingrowth of the tissue structure into porous surface 45 of attachment plate 44D. The close proximity of apertures 46 to attachment plate 44D facilitates more direct contact between the tissue structure and attachment plate 44D. Moreover, recesses 68, 70, facilitate easier suture passage through apertures 46 and the corresponding throughbores 48 due to the thinness of throughbores 48 (width W). Also, recesses 68, 70, facilitate passage of a curved suture needle through throughbores 48 due to the thinness of throughbores 48 (width W).

Referring next to FIGS. 18-21, yet another embodiment proximal tibial implant 30E is shown and may be substantially identical to proximal tibial implant 30, described above with reference to FIGS. 1-5, proximal tibial implant 30A, described above with reference to FIGS. 6-8, proximal tibial implant 30B, described above with reference to FIG. 9, proximal tibial implant 30C, described above with reference to FIG. 10, or proximal tibial implant 30D, described above with reference to FIGS. 11-12, except as described below. Proximal tibial implant 30E includes body 32, bearing surface 34, mating structure 36, rotational adjustment tabs 38, distal end 40, and proximal end 42. Proximal tibial implant 30E also includes attachment plate 44E which may be similar to attachment plate 44, described above with reference to FIGS. 1-5, attachment plate 44A, described above with reference to FIGS. 6-8, attachment plate 44B, described above with reference to FIG. 9, attachment plate 44C, described above with reference to FIG. 10, or attachment plate 44D, described above with reference to FIGS. 11-12, except as described below. For example, attachment plate 44E on the anterior surface of proximal tibial implant 30E includes porous surface 45 to facilitate ingrowth of a tissue structure.

Figure 19:
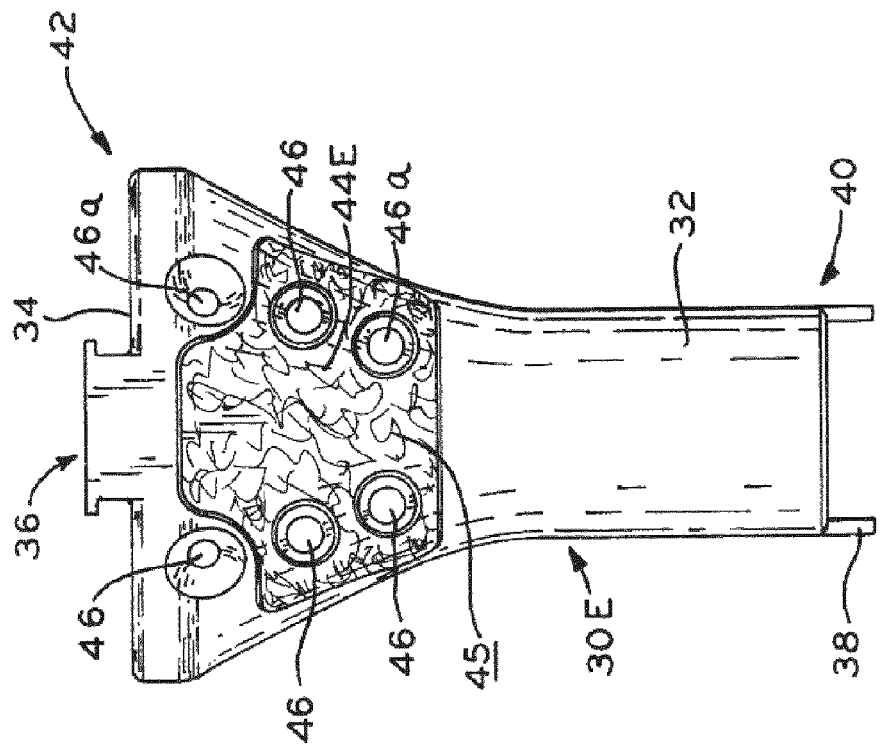
FIG. 19 is an anterior elevational view of the proximal tibial implant of FIG. 18.
Figure 18:
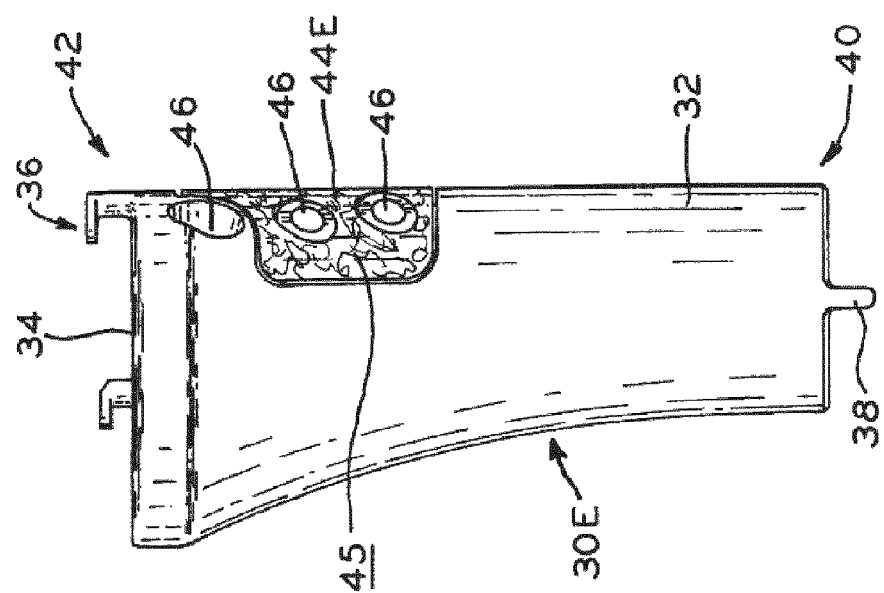
FIG. 18 is a side elevational view of a proximal tibial implant according to still yet another exemplary embodiment of the present disclosure.

As shown in FIG. 19, attachment plate 44E surrounds some, but not all, suture apertures 46. As discussed above with reference to FIG. 9, reducing and/or eliminating contact between the sutures that extend through apertures 46 and the rough, uneven porous surface 45 of attachment plate 44E reduces the likelihood that the sutures will weaken or tear.

In operation, a surgeon may attach a tissue structure to proximal tibial implant 30E. First, the surgeon positions the tissue structure in contact with attachment plate 44E. At least one suture is then threaded through apertures 46 and the corresponding throughbores 48 to maintain contact between the tissue structure and attachment plate 44E. The surgeon may select any or all apertures 46 and the corresponding throughbores 48 to secure the tissue structure to proximal tibial implant 30E. In one embodiment, the sutures may be biodegradable after a period of time in which the tissue structure is permanently attached to proximal tibial implant 30E via ingrowth of the tissue structure into porous surface 45 of attachment plate 44E. The close proximity of apertures 46 to attachment plate 44E facilitates more direct contact between the tissue structure and attachment plate 44E. At the same time, providing a non-porous area around at least some apertures 46, 46a, reduces contact between the sutures and the rough, uneven porous surface 45, which could tear the sutures.

Referring next to FIGS. 23-34, still yet another embodiment proximal tibial implant 30F is shown and may be substantially identical to proximal tibial implant 30, described above with reference to FIGS. 1-5, proximal tibial implant 30A, described above with reference to FIGS. 6-8, proximal tibial implant 30B, described above with reference to FIG. 9, proximal tibial implant 30C, described above with reference to FIG. 10, proximal tibial implant 30D, described above with reference to FIGS. 11-12, or proximal tibial implant 30E, described above with reference to FIGS. 18-21, except as described below. Proximal tibial implant 30F includes body 32, bearing surface 34, mating structure 36, rotational adjustment tabs 38, distal end 40, and proximal end 42. Proximal tibial implant 30E also includes attachment plate 44F which may be similar to attachment plate 44, described above with reference to FIGS. 1-5, attachment plate 44A, described above with reference to FIGS. 6-8, attachment plate 44B, described above with reference to FIG. 9, attachment plate 44C, described above with reference to FIG. 10, attachment plate 44D, described above with reference to FIGS. 11-12, or attachment plate 44E, described above with reference to FIGS. 18-21, except as described below. For example, attachment plate 44F on the anterior surface of proximal tibial implant 30F includes porous surface 45 to facilitate ingrowth of a tissue structure. As shown by comparing FIGS. 23 and 24, attachment plate 44F is a modular component set into recess 43 of body 32 and attached to body 32, such as via diffusion bonding.

Figure 23:
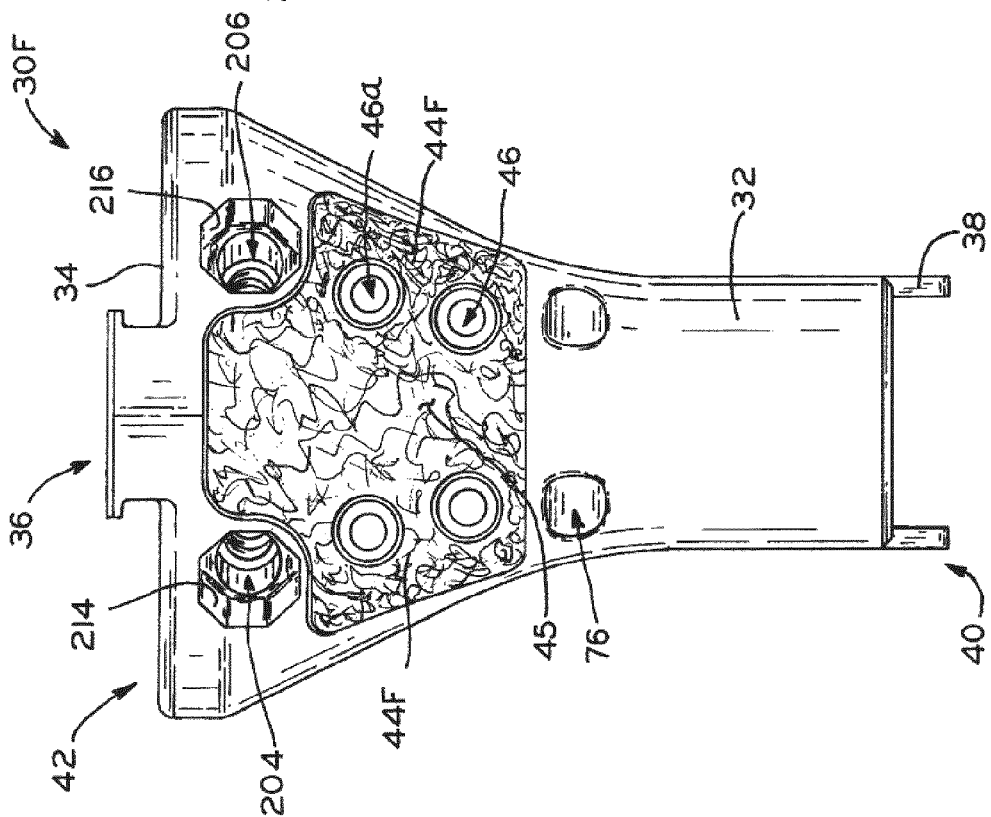
FIG. 23 is an anterior elevational view of a proximal tibial implant according to an exemplary embodiment of the present disclosure including a tissue attachment plate.
Figure 25:
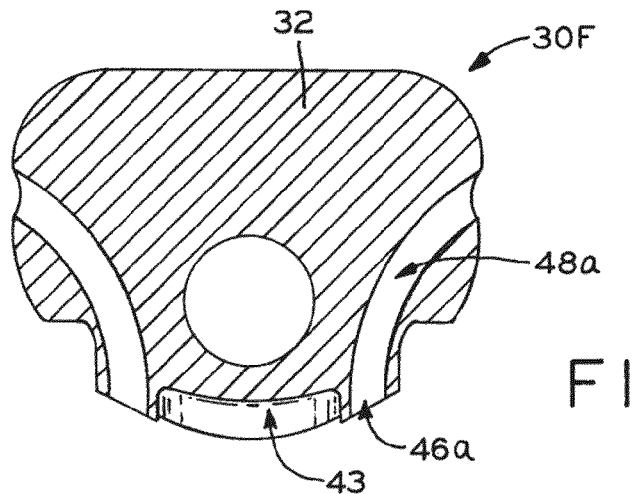
FIG. 25 is a cross-sectional view of the proximal tibial implant of FIG. 24, taken along line 25-25 of FIG. 24.
Figure 26:
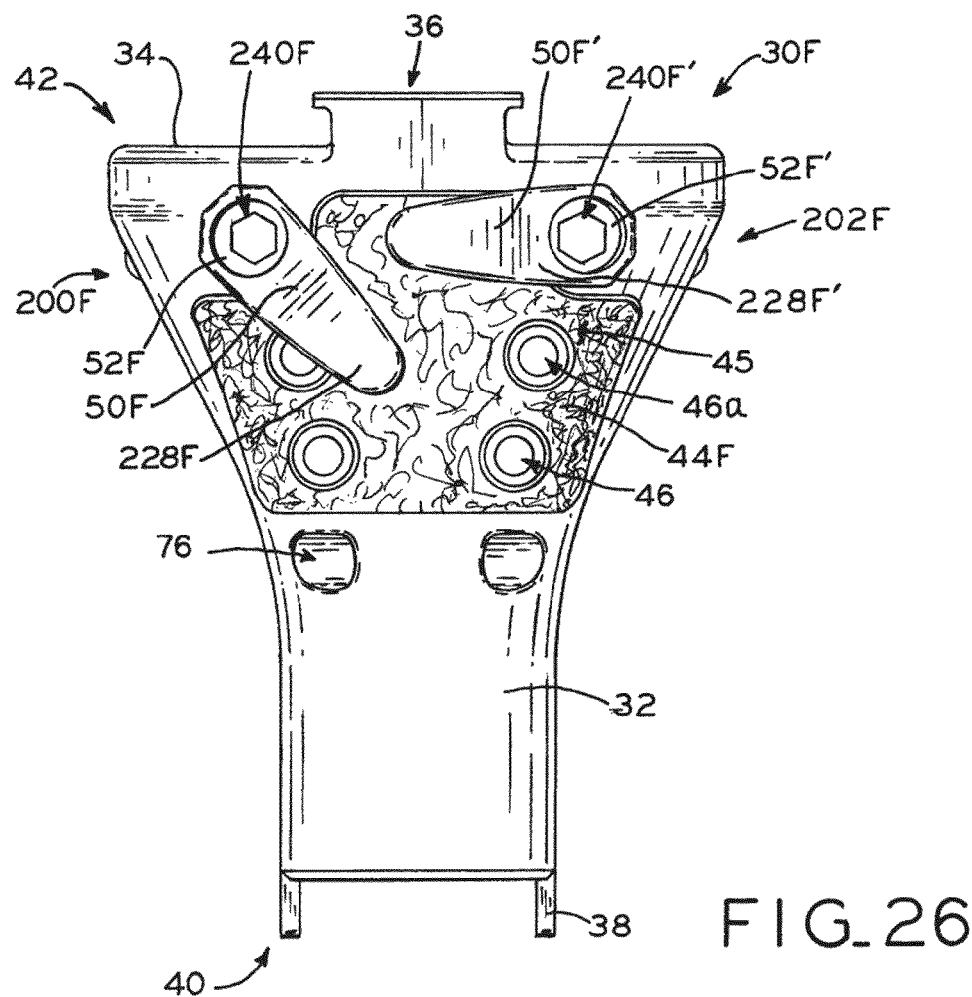
FIG. 26 is an anterior elevational view of the proximal tibial implant of FIG. 23, further including a medial rotating fixation structure and a lateral rotating fixation structure, each having a washer and a fastener.
Figure 32:
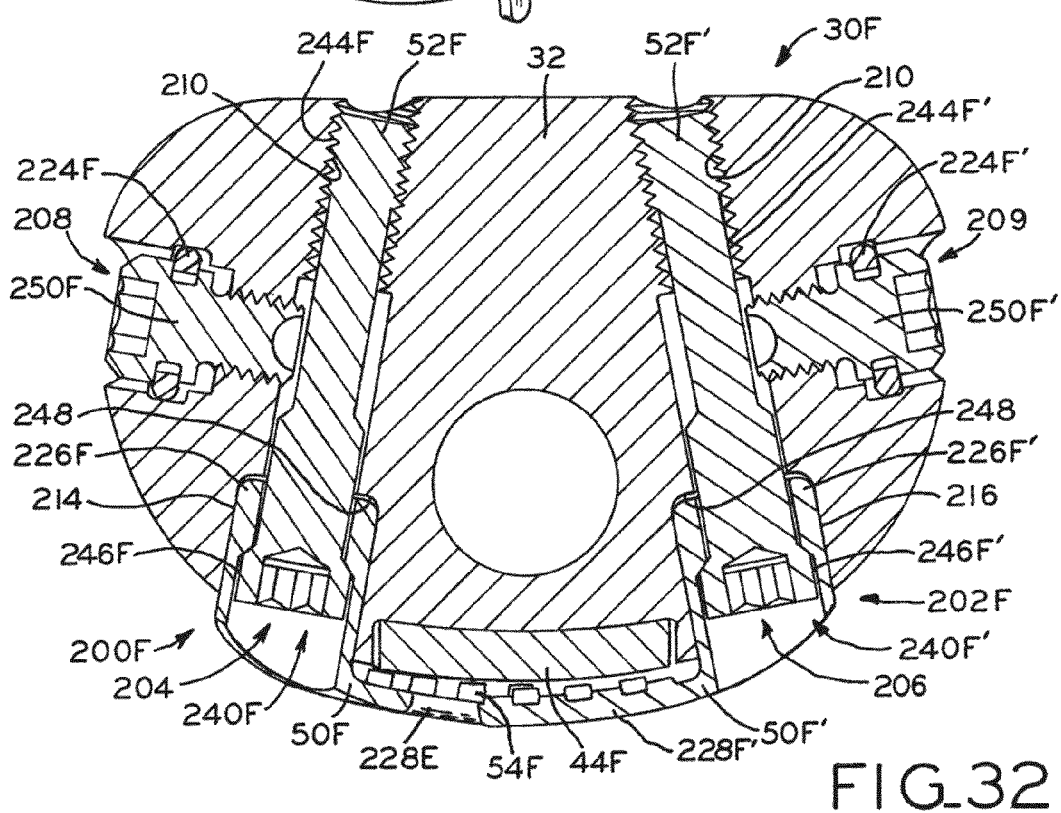
FIG. 32 is a cross-sectional view of the proximal tibial implant of FIG. 31, taken along line 32-32 of FIG. 31.

Referring to FIG. 26, proximal tibial implant 30F also includes medial fixation structure 200F and lateral fixation structure 202F. Proximal tibial implant 30F includes medial bore 204 that is sized to receive medial fixation structure 200F and lateral bore 206 that is sized to receive lateral fixation structure 202F, as shown in FIG. 23. It is within the scope of the present invention that fixation structures 200F, 202F, may be labeled to ensure that medial fixation structure 200F is inserted into body 32 medially of lateral fixation structure 202F. Also, each fixation structure 200F, 202F, may be sized or shaped to fit into only its corresponding bore 204, 206, to ensure that medial fixation structure 200F is inserted into body 32 medially of lateral fixation structure 202F. Walls 214, 216, that define bores 204, 206, respectively, may include various features to cooperate with fixation structures 200F, 202F. For example, walls 214, 216, may define a polygonal, or non-circular, bore 204, 206, such as the octagonal bores 204, 206, shown in FIG. 23. As another example, walls 214, 216, may include internal threads 210 and/or shoulder 248, as shown in FIG. 32. Proximal tibial implant 30F also includes cross bores 208, 209, which are described further below.

Medial fixation structure 200F is illustrated in FIG. 28 and includes washer 50F and fastener 52F. Washer 50F is an essentially L-shaped structure that includes body portion 226F and tissue engagement arm 228F that extends substantially perpendicular to body portion 226F. As shown in FIG. 27, tissue engagement arm 228F of washer 50F is slightly arcuate to match the contour of body 32. Body portion 226F of washer 50F defines bore 240F that is configured to receive fastener 52F. Fastener 52F may include any suitable fastening mechanism, including an anchor or a mechanism that expands once inserted into body 32 of proximal tibial implant 30F. For example, fastener 52F may be a screw or bolt having external thread 244F and head 246F, as shown in FIG. 28.

A plurality of teeth 54F extends from washer 50F, and specifically from tissue engagement arm 228F of washer 50F. Teeth 54F may be arranged in various patterns. For example, teeth 54F may be aligned in columns and rows, teeth 54F may be aligned diagonally, or teeth 54F may be distributed randomly across the surface of washer 50F. Adjacent teeth 54F may be separated by approximately 1 mm, 2 mm, 3 mm, or more, for example. According to an exemplary embodiment of the present disclosure, and as shown in FIG. 27, each tooth 54F includes at least one face, referred to herein as blocking face 232F, that extends substantially normal to engagement arm 228F of washer 50F and/or body 32 of proximal tibial implant 30F, as discussed in more detail below. Blocking faces 232F of teeth 50F may all face the same direction, as shown in FIG. 27, or blocking faces 232F of teeth 50F may face different directions.

Lateral fixation structure 202F includes washer 50F' and fastener 52F'. Washer 50F' may be substantially identical to washer 50F described above with respect to FIGS. 27-28, or washer 50F' may be a mirror image of washer 50F, for example. Also, fastener 52F' may be substantially identical to fastener 52F described above with respect to FIG. 28.

In operation, a surgeon may attach a tissue structure to proximal tibial implant 30F. Prior to permanently attaching the tissue structure to proximal tibial implant 30F, the surgeon may gather and temporarily attach the tissue structure to proximal tibial implant 30F. In one embodiment, the surgeon first gathers or collects the desired tissue structure. Then, the surgeon positions at least one suture or other surgical fastener through aperture 76 and its associated throughbore to temporarily hold the tissue structure in place. Because the attachment through aperture 76 may be only temporary, aperture 76 need not be surrounded by porous surface 45.

Next, the surgeon positions the tissue structure in contact with attachment plate 44F and clamps the tissue structure against attachment plate 44F using fixation structures 200F, 202F. An exemplary method of clamping the tissue structure with fixation structures 200F, 202F, is set forth in the following paragraphs.

First, the surgeon selects desired fixation structures 200F, 202F, from a set provided. The set may include, for example, washers 50F, 50F', of various sizes and washers 50F, 50F', having various arrangements of teeth 54F, 54F'. According to an exemplary embodiment of the present disclosure, body portions 226F, 226F', of washers 50F, 50F', and/or fasteners 52F, 52F', may be provided in various lengths to alter the final distance between engagement arms 228F, 228F', of washers 50F, 50F', and body 32 of proximal tibial implant 30F. This distance may impact the clamping force applied by washers 50F, 50F', to the tissue structure and the space available for the tissue structure. Therefore, depending on the desired clamping force, the amount of tissue to be attached, and other considerations, the distance between engagement arms 228F, 228F', of washers 50F, 50F', and body 32 of proximal tibial implant 30F may vary. For example, the distance between engagement arms 228F, 228F', of washers 50F, 50F', and body 32 of proximal tibial implant 30F may vary between approximately 1 mm, 2 mm, 3 mm, 4 mm, 5 mm, or more.

Next, the surgeon aligns the selected washers 50F, 50F', relative to body 32 and inserts washers 50F, 50F', into bores 204, 206, of proximal tibial implant 30F. The surgeon may rotate each washer 50F, 50F', at various angles relative to body 32, as shown in FIG. 26. According to an exemplary embodiment of the present disclosure, the surgeon may align washers 50F, 50F', to substantially cover the tissue structure with engagement arms 228F, 228F', of washers 50F, 50F'. In other words, the surgeon may align washers 50F, 50F', to maximize contact between engagement arms 228F, 228F', of washers 50F, 50F', and the tissue structure. For example, as shown in FIG. 26, medial washer 50F may be angled relative to body 32 to cross over a medial gastrocnemius flap that is wrapped across proximal tibial implant 30F. According to another exemplary embodiment of the present disclosure, the surgeon may rotate washers 50F, 50F', to resist movement or retraction of the tissue structure with teeth 54F, 54F', and specifically blocking faces 232F, 232F', of teeth 54F, 54F'. In the illustrated embodiment, each washer 50F, 50F', may be rotated to eight different positions due to the octagonal shape of bores 204, 206, and the corresponding octagonal shape of body portion 226F, 226F', of washers 50F, 50F'. The number of available positions may be increased or decreased by varying the shape of bores 204, 206, and washers 50F, 50F'.

After aligning washers 50F, 50F', with proximal tibial implant 30F, the surgeon secures washers 50F, 50F', to proximal tibial implant 30F using fasteners 52F, 52F', and set screws 250F, 250F'. Referring to the illustrated embodiment of FIG. 32, fasteners 52F, 52F', are first inserted through bores 240F, 240F', of washers 50F, 50F', and posteriorly into bores 204, 206, in body 32 of proximal tibial implant 30F. Eventually, external threads 244F, 244F' of fasteners 52F, 52F', engage internal threads 210 of bores 204, 206. In this arrangement, heads 246F, 246F', of fasteners 52F, 52F', prevent washers 50F, 50F', from withdrawing from bores 204, 206, and shoulders 248 of walls 214, 216, prevent washers 50F, 50F', from retracting into bores 204, 206. Therefore, each washer 50F, 50F', is able to maintain a fixed axial spacing from body 32. Also, the keyed engagement between octagonal body portions 226F, 226F', of washers 50F, 50F', and octagonal walls 214, 216, prevent washers 50F, 50F', from spinning freely in bores 204, 206. Fasteners 52F, 52F', may be secured in bores 204, 206, at a desired depth by inserting set screws 250F, 250F', medially and laterally into cross bores 208, 209, in body 32 of proximal tibial implant 30F to contact the posteriorly extending fasteners 52F, 52F'. Optionally, set screws 250F, 250F', may include snap rings 224F, 224F', as shown in FIG. 32, to enhance the connection between set screws 250F, 250F', and body 32 of proximal tibial implant 30F.

Figure 31:
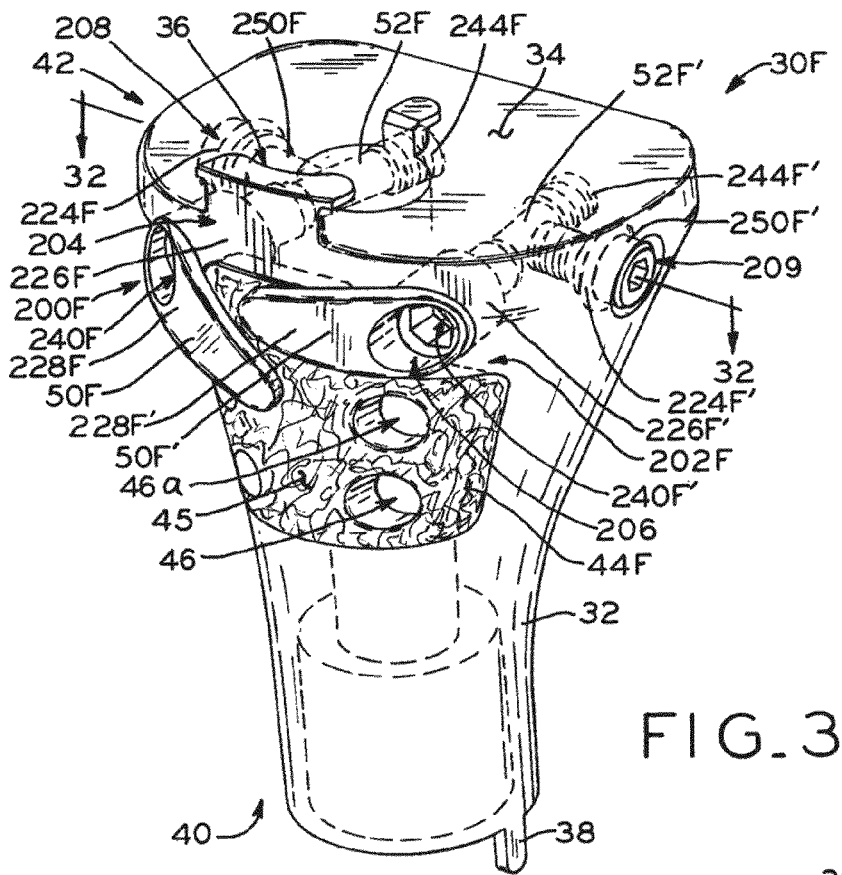
FIG. 31 is a perspective view of the proximal tibial implant of FIG. 26, further including a set screw and a snap ring.

According to an exemplary embodiment of the present disclosure, the tissue structure should be held tightly in contact with the anterior attachment plate 44F of proximal tibial implant 30F beneath washers 50F, 50F'. More particularly, the tissue structure should be held tightly in contact with the anterior attachment plate 44F of proximal tibial implant 30F beneath engagement arms 228F, 228F', of washers 50F, 50F'. Thus, the bottom surfaces of engagement arms 228F, 228F', of washers 50F, 50F', act as clamping surfaces. According to another exemplary embodiment of the present disclosure, washers 50F, 50F', should permit adequate circulation and fluid flow through the tissue structure. Thus, teeth 54F, 54F', on washers 50F, 50F', may be oriented to resist movement of the tissue structure, but adjacent teeth 54F, 54F', may be separated to permit blood and fluid to flow between adjacent teeth 54F, 54F'. For example, adjacent teeth 54F, 54F', may be separated by approximately 1 mm, 2 mm, 3 mm, or more. Also, as shown in FIG. 31, washers 50F, 50F', themselves are separated on the anterior surface of proximal tibial implant 30F to permit blood and fluid to flow between washers 50F, 50F'. Optionally, if washers 50F, 50F', provide too much or too little clamping pressure against the tissue structure, fixation structures 200F, 202F, may be removed and replaced with fixation structures 200F, 202F, of a different size. For example, if washers 50F, 50F', provide too much clamping pressure against the tissue structure, fixation structures 200F, 202F, may be removed and replaced with fixation structures 200F, 202F, having longer body portions 226F, 226F', and/or longer fasteners 52F, 52F'. Washers 50F, 50F', provide a mechanical fixation between the tissue structure and proximal tibial implant 30F. Over time, the tissue structure may grow into attachment plate 44F. Thus, the tissue structure may be both biologically and mechanically affixed to proximal tibial implant 30F.

Figure 29:
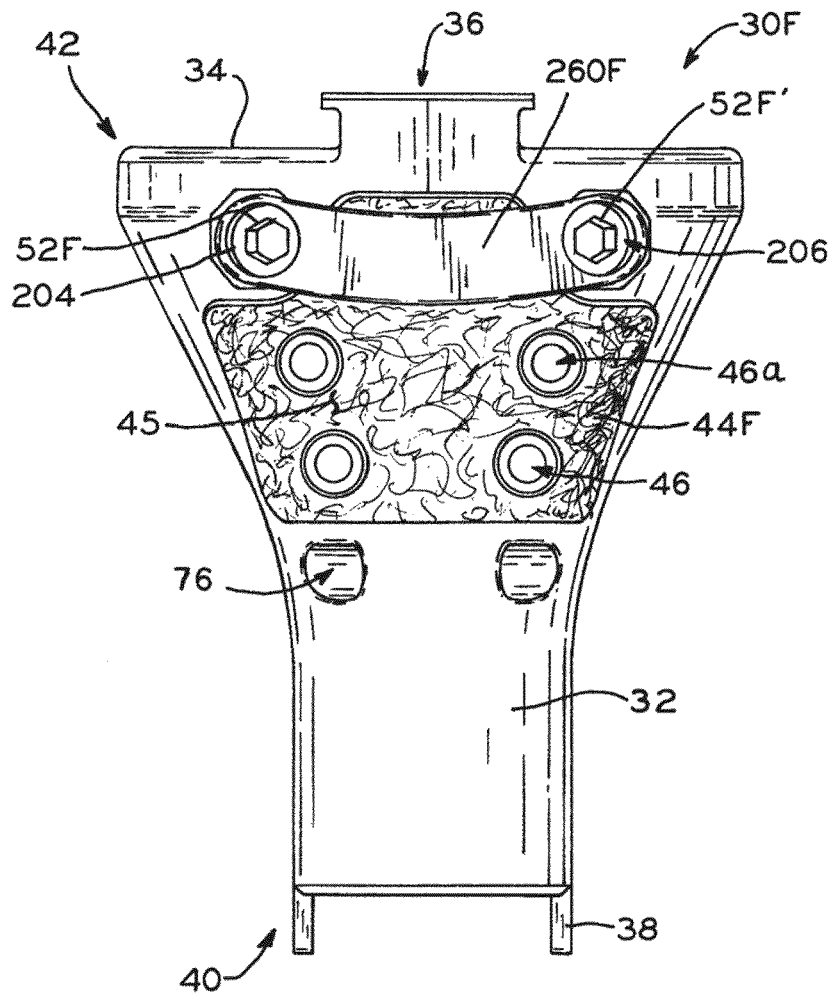
FIG. 29 is an anterior elevational view of the proximal tibial implant of FIG. 23, further including a bar in place of the washers of FIG. 26.
Figure 30:
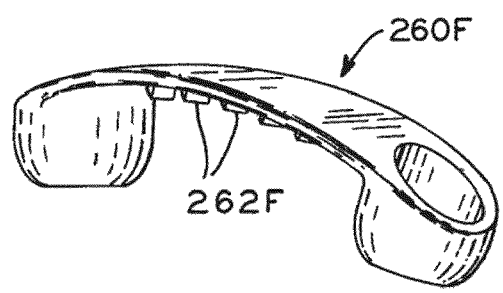
FIG. 30 is a perspective view of the bar of FIG. 29.

In certain situations, the surgeon may replace the two individual washers 50F, 50F', of FIG. 26 with the single bar 260F shown in FIGS. 29-30. Bar 260F spans medially-laterally across anterior attachment plate 44F from bore 204 to bore 206. Bar 260F may be secured to body 32 using the same fasteners 52F, 52F', that are used to secure washers 50F, 50F', to body 32. Like washers 50F, 50F', bar 260F includes a plurality of teeth 262F that are configured to engage and clamp the tissue structure against anterior attachment plate 44F. Bar 260F may have a straight configuration or a bowed configuration, as shown in FIG. 30.

Also, the surgeon may secure the tissue structure to the porous attachment plate 44F by threading sutures through any or all apertures 46, 46a, and the corresponding throughbores 48, 48a. In one embodiment, the sutures may be biodegradable after a period of time in which the tissue structure is permanently attached to proximal tibial implant 30F via ingrowth of the tissue structure into attachment plate 44F.

Referring next to FIGS. 13-17, proximal femoral implant 80 is shown and may be used to restore mechanical and biological fixation of tissue associated with a hip joint of a patient to enhance the stability of the hip joint, to restore hip joint function, and to enhance hip joint kinematics. Proximal femoral implant 80 may typically be used in a patient requiring complete metaphyseal removal of the proximal femur.

Proximal femoral implant 80 includes body 82 having proximal end 92 and distal end 90. Body 32 also includes an anterior surface, a posterior surface opposite the anterior surface, a lateral surface, and a medial surface opposite the lateral surface. As shown in FIG. 16, proximal femoral implant 80 defines a generally slender profile with no protruding edges or structures in the anterior or posterior directions. The slender profile also tapers proximally toward proximal end 92 from distal end 90 which facilitates soft tissue closure after a procedure is completed and prevention of potential damage to subcutaneous tissue. Also, proximal femoral implant 80 may include a modular or integral neck 84 configured to mate with a corresponding femoral head component (not shown) of a prosthetic hip joint. In turn, the femoral head component may articulate against a natural or a prosthetic acetabulum (not shown).

Proximal femoral implant 80 further includes anteversion adjustment tabs 88 at distal end 90 to allow for in vivo rotational adjustment of proximal femoral implant 80 relative to a prosthetic femoral stem component or the natural femur. Anteversion adjustment tabs 88 may generally extend distally from body 82 along a lateral and/or a medial side of proximal femoral implant 80. A plurality of tabs 88 may be utilized or a single tab 88 may be utilized.

The medial side of proximal femoral implant 80 includes medial protrusion 86 that projects medially from body 82. More particularly, medial protrusion 86 projects radially from the substantially cylindrical body 82. According to an exemplary embodiment of the present invention, medial protrusion 86 projects approximately 6 mm, 8 mm, 10 mm, 12 mm, 14 mm, 16 mm, or more, from the substantially cylindrical body 82. Medial protrusion 86 includes porous surface 96, which may be an inlay of porous material substantially identical to porous surface 45 described above. Porous surface 96 may be formed integrally with medial protrusion 86 or, alternatively, porous surface 96 may be formed on a plate which is attached to medial protrusion 86. Medial protrusion 86 also includes a plurality of apertures 98 having corresponding throughbores 99 (FIG. 16) that extend anteriorly-posteriorly through medial protrusion 86. Medial protrusion 86 serves to replicate the lesser trochanter of the natural proximal femur. Therefore, like the natural lesser trochanter, medial protrusion 86, and the corresponding throughbores of apertures 98 extending therethrough, may provide a secure attachment to tissue structures located medially of proximal femoral implant 80, including the iliopsoas muscles. Also, as shown in FIG. 17, medial protrusion 86 buttresses neck 84, which may provide additional support to proximal femoral implant 80 when implanted into a hip joint.

The lateral side of proximal femoral implant 80 includes lateral ingrowth pads 102, 104, attached to body 82 via fasteners 103, 105, respectively. Although each lateral ingrowth pad 102, 104, is shown with only a single fastener 103, 105, respectively, each lateral ingrowth pad 102, 104, may be configured to receive multiple fasteners. The use of multiple fasteners prevents lateral ingrowth pads 102, 104, from rotating and/or spinning freely relative to body 82.

Figure 14:
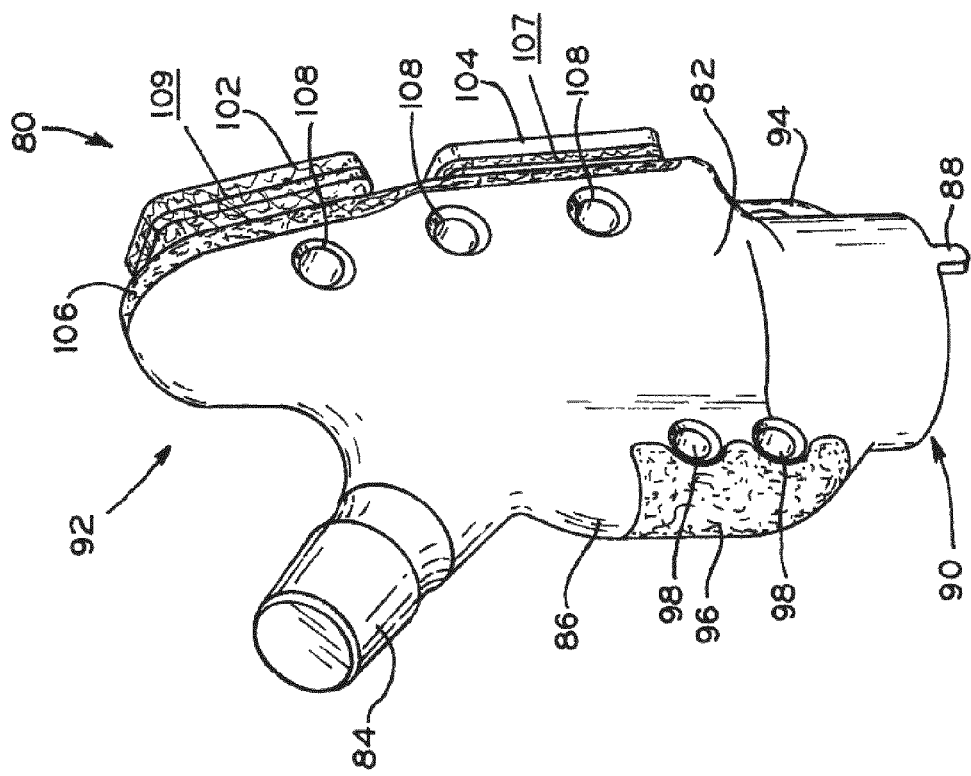
FIG. 14 is another perspective view of the proximal femoral implant of FIG. 13.
Figure 13:
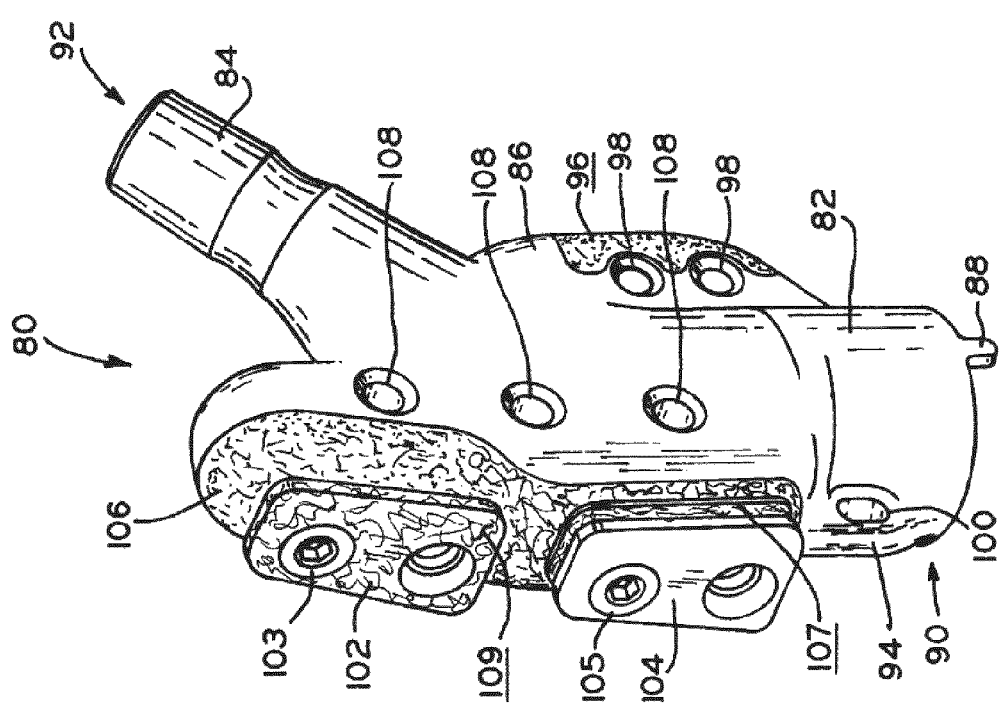
FIG. 13 is a perspective view of a proximal femoral implant according to an exemplary embodiment of the present disclosure.

Each lateral ingrowth pad 102, 104, may include porous surface 109, 107, respectively. Porous surface 109, 107, may be substantially identical to porous surface 45 described above. Lateral ingrowth pads 102, 104, may be constructed entirely of a porous material. For example, lateral ingrowth pad 102 is illustrated in FIGS. 13-15 as being constructed entirely of a porous material, such that porous surface 109 substantially covers lateral ingrowth pad 102. Alternatively, lateral ingrowth pads 102, 104, may include a porous material bonded to or coated onto a solid metal substrate. For example, lateral ingrowth pad 104 is illustrated in FIGS. 13-15 as being constructed of porous material bonded to a solid metal substrate, such that porous surface 107 is positioned adjacent to porous surface 106 of body 82. Also, lateral ingrowth pads 102, 104, may be slightly angled to follow the path of body 82. For example, as shown in FIG. 15, the proximal end of lateral ingrowth pad 102 is more medially positioned than the distal end of lateral ingrowth pad 102. The angle of lateral ingrowth pad 102, in particular, facilitates prevention of potential irritation of subcutaneous tissue surrounding the proximal lateral portion of proximal femoral implant 80 after implantation.

The lateral side of proximal femoral implant 80 further includes lateral porous surface 106 positioned beneath lateral ingrowth pads 102, 104. Like medial porous surface 96, lateral porous surface 106 may be substantially identical to porous surface 45 described above. For example, like porous surface 45, lateral porous surface 106 may be impregnated with and/or coated with biologically active agents. Porous surface 106 may substantially wrap around the proximal lateral end of body 82 from an anterior to a posterior side of body 82 to provide optimal attachment surfaces for tissue structures, as described below. Although porous surface 106 is illustrated as a continuous surface that extends along the lateral side of body 82 from proximal end 92 toward distal end 90, it is within the scope of the present disclosure that porous surface 106 may include multiple, distinct porous segments on the lateral side of body 82.

As shown in FIGS. 15-17, the lateral side of body 82 further includes a plurality of lateral apertures 108 having corresponding throughbores that extend through body 82 from an anterior side to a posterior side. Also, lateral protrusion 94 extends laterally from body 82 and includes aperture 100 having a corresponding throughbore 101.

In operation, a surgeon may attach tissue structures to proximal femoral implant 80. The tissue structures may include soft tissue structures, such as muscles, ligaments, capsules, and tendons. The tissue structures may also include bone, including bone that retains a natural connection to muscles, ligaments, capsules, or tendons. Prior to permanently attaching the tissue structures to proximal femoral implant 80, the surgeon may gather and temporarily attach the tissue structures to proximal femoral implant 80. In one embodiment, the surgeon first gathers or collects the desired tissue structures. Then, the surgeon positions at least one suture or other surgical fastener through aperture 100 and the corresponding throughbore 101 (FIG. 17) in lateral protrusion 94 to temporarily hold the tissue structures in place. Because the attachment through throughbore 101 may be only temporary, lateral protrusion 94 of proximal femoral implant 80 need not include a porous surface.

To attach a tissue structure to the medial side of proximal femoral implant 80, a surgeon positions the tissue structure in contact with porous surface 96 on medial protrusion 86. At least one suture or other surgical fastener, such as surgical tape or surgical cable, is then threaded through one or both apertures 98 and through corresponding throughbores 99 to secure the tissue structure to proximal femoral implant 80 and to maintain contact between the tissue structure and porous surface 96. In one embodiment, the sutures may be biodegradable after a period of time in which the tissue structure is permanently attached to proximal femoral implant 80 via ingrowth of the tissue structure into porous surface 96. The close proximity of apertures 98 to porous surface 96 facilitates more direct contact between the tissue structure and porous surface 96, thereby enhancing ingrowth of the tissue structure into porous surface 96. In an exemplary embodiment, the tissue structure is an iliopsoas muscle which, when attached to proximal femoral implant 80, enhances stability of the hip joint. In this embodiment, medial apertures 98 provide locations from which tissue structures are pulled into contact with the medial side of proximal femoral implant 80, similar to the natural lesser trochanter.

To attach a tissue structure to the lateral side of proximal femoral implant 80, the surgeon positions the tissue structure in contact with porous surface 106. At least one suture or other surgical fastener is then threaded through at least one aperture 108 and the corresponding throughbore proximate to porous surface 106 to secure the tissue structure to proximal femoral implant 80 and to maintain contact between the tissue structure and porous surface 106. In one embodiment, the sutures may be biodegradable after a period of time in which the tissue structure is permanently attached to proximal femoral implant 80 via ingrowth of the tissue structure into porous surface 106. The close proximity of apertures 108 to porous surface 106 facilitates more direct contact between the tissue structure and porous surface 106. In an exemplary embodiment, the tissue structure is an abductor muscle, including at least one of the gluteus maximus, the gluteus medius, the gluteus minimus, and the tensor fascia lata, and/or a quadriceps muscle which, when attached to proximal femoral implant 80, enhances the kinematics of the hip joint. In this embodiment, lateral apertures 108 provide locations from which tissue structures are pulled into contact with the lateral side of proximal femoral implant 80 and facilitate providing a sling around proximal femoral implant 80 to maximize hip joint function and kinematics.

To further attach a tissue structure to the lateral side of proximal femoral implant 80, the surgeon may tighten lateral ingrowth pads 102, 104, against body 82 of proximal femoral implant 80. In an exemplary procedure, a surgeon pulls or otherwise manipulates a tissue structure in close proximity to porous surface 106 and then tightens fasteners 103, 105, into body 82 to clamp lateral ingrowth pads 102, 104, against the tissue structure. Using this exemplary procedure, the tissue structure may become mechanically fixed to proximal femoral implant 80. Also, over time, the tissue structure may grow into porous surface 109 of lateral ingrowth pad 102, porous surface 107 of lateral ingrowth pad 104, and/or porous surface 106 of body 82.

Although not illustrated in FIGS. 13-17, proximal femoral implant 80 may also use at least one rotatable fixation structure similar to washers 50, 50', described above with respect to FIGS. 6-8, to mechanically fix a tissue structure to proximal femoral implant 80 and to facilitate grasping and pulling a tissue structure into contact with proximal femoral implant 80.

Figure 22:
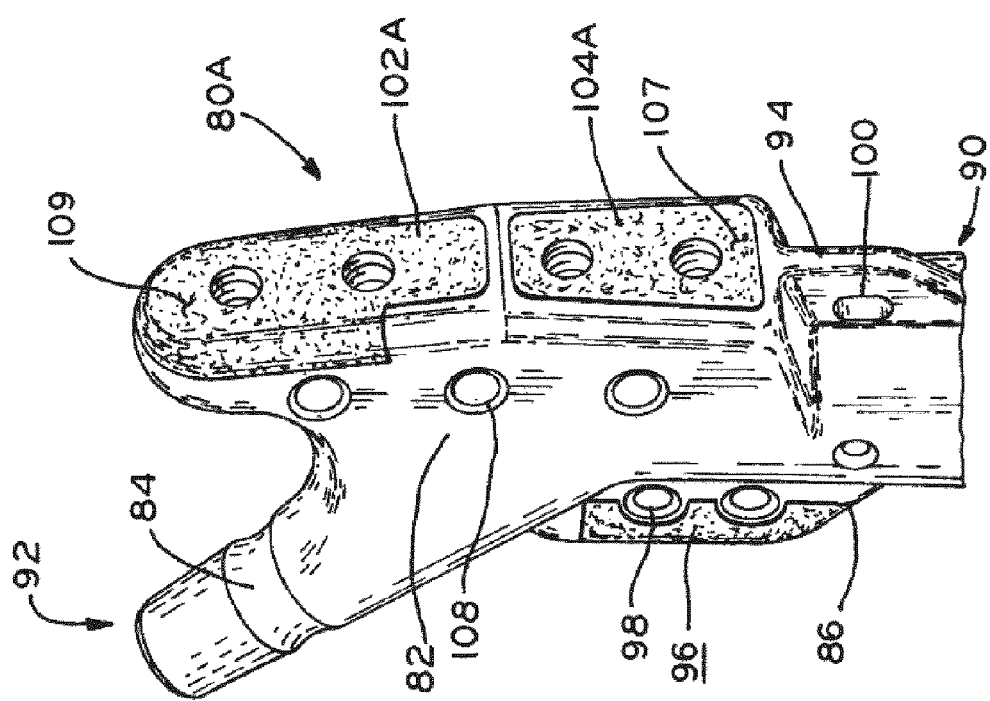
FIG. 22 is a perspective view of a proximal femoral implant according to another exemplary embodiment of the present disclosure.
Figure 24:
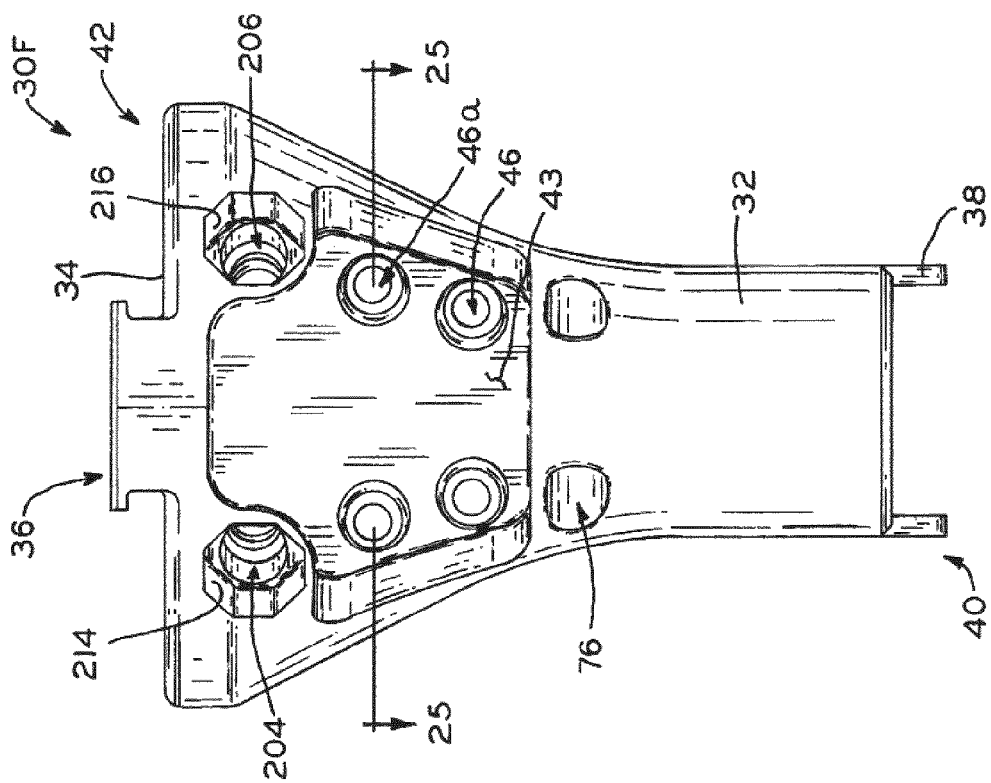
FIG. 24 is an anterior elevational view of the proximal tibial implant of FIG. 23 shown without the tissue attachment plate.

Referring now to FIG. 22, another embodiment proximal femoral implant 80A is shown and may be substantially identical to proximal femoral implant 80, described above with reference to FIGS. 13-17, except as described below. Proximal femoral implant 80A includes body 82, neck 84, adjustment tabs (not shown), medial protrusion 86, lateral protrusion 94, distal end 90, and proximal end 92. The medial side of proximal femoral implant 80A includes porous surface 96 and a plurality of apertures 98 defining corresponding throughbores in body 82. The lateral side of proximal femoral implant 80A includes lateral ingrowth pads 102A, 104A, and a plurality of lateral apertures 108 defining corresponding throughbores in body 82. Lateral ingrowth pads 102A, 104A, may be substantially identical to lateral ingrowth pads 102, 104, described above with reference to FIGS. 13-17, except as described below.

As shown in FIG. 22, lateral ingrowth pads 102A, 104A, are constructed entirely of a porous material, such that porous surfaces 109, 107, substantially cover lateral ingrowth pads 102A, 104A, respectively. Lateral ingrowth pads 102A, 104A, may be modular components that are attached to body 82 via one or more fasteners (not shown) inserted through lateral ingrowth pads 102A, 104A, and into body 82. The fastener may include a screw, bolt, anchor mechanism, a mechanism which expands once inserted into body 82, or any other suitable fastening mechanism. Lateral ingrowth pads 102A, 104A, may be inset into body 82, such as received within a recess of body 82. When lateral ingrowth pads 102A, 104A, are attached to body 82, porous surfaces 109, 107, of lateral ingrowth pads 102A, 104A, may be substantially flush with the remainder of the proximal femoral implant 80A.

In operation, a surgeon may attach tissue structures to proximal femoral implant 80A. To attach a tissue structure to the medial side of proximal femoral implant 80A, the surgeon may follow the same process described above with respect to proximal femoral implant 80 of FIGS. 13-17. For example, the surgeon may place the tissue structure in contact with porous surface 96 on medial protrusion 86 of proximal femoral implant 80A and secure the tissue structure in place by threading sutures through apertures 98 and the corresponding throughbores. To attach a tissue structure to the lateral side of proximal femoral implant 80A, the surgeon positions the tissue structure in contact with one or more of porous surfaces 109, 107. In one embodiment, the attachment to porous surfaces 109, 107, may be maintained by threading at least one suture or other surgical fastener through at least one aperture 108 and its associated throughbore. In another embodiment, the attachment to porous surfaces 109, 107, may be maintained by placing the tissue structure between lateral ingrowth pads 102A, 104A, and body 82. Tightening lateral ingrowth pads 102A, 104A, against body 82 of proximal femoral implant 80A clamps and holds the tissue structure between lateral ingrowth pads 102A, 104A, and body 82. As shown in FIG. 22, lateral ingrowth pads 102A, 104A, may be constructed of a material that allows tissue and blood vessels to grow through the plate. In another embodiment, a tissue structure may be held against lateral ingrowth pads 102A, 104A, using sutures or a muscle, for example.

Referring now to FIGS. 35-43, yet another embodiment proximal femoral implant 80B is shown and may be substantially identical to proximal femoral implant 80, described above with reference to FIGS. 13-17, or proximal femoral implant 80A, described above with reference to FIG. 22, except as described below. Proximal femoral implant 80B includes body 82, adjustment tabs 88, medial protrusion 86, lateral protrusion 94, distal end 90, and proximal end 92. Body 82 receives modular neck 84B that is configured to mate with a corresponding femoral head component (not shown) of a prosthetic hip joint. The medial side of proximal femoral implant 80B includes porous surface 96 and a plurality of apertures 98 defining throughbores in body 82. The lateral side of proximal femoral implant 80B includes porous surfaces 106, 106', and a plurality of lateral apertures 108 defining throughbores in body 82.

Additionally, proximal femoral implant 80B includes proximal fixation structure 300 and distal fixation structure 302. Proximal femoral implant 80B includes proximal bore 304 that is sized to receive proximal fixation structure 300 and distal bore 306 that is sized to receive distal fixation structure 302. Walls 314, 316, that define bores 304, 306, respectively, may include various features to cooperate with fixation structures 300, 302, respectively. For example, walls 314, 316, may define a polygonal, or non-circular, bore 304, 306, such as the octagonal bores 304, 306, shown in FIG. 35. As another example, walls 314, 316, may include internal threads 310, annular indentation 312, and/or shoulder 348, as shown in FIG. 43.

Figure 38:
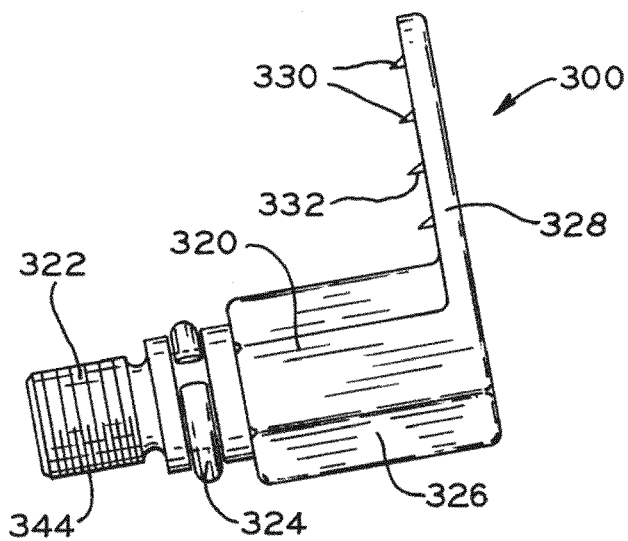
FIG. 38 is an elevational view of the proximal rotating fixation structure of FIG. 36.
Figure 39:
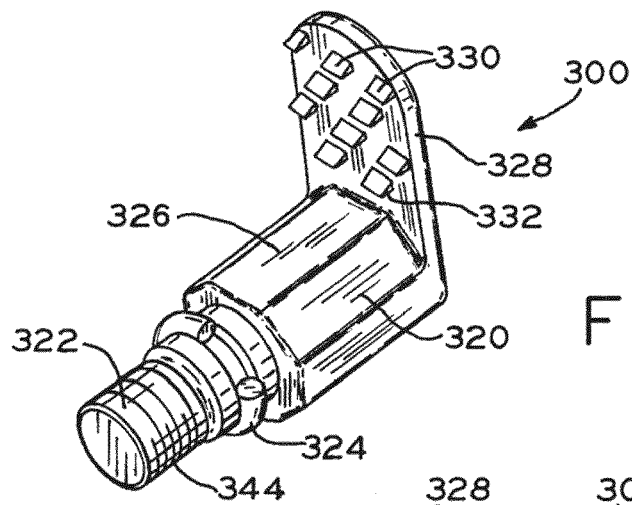
FIG. 39 is a perspective view of the proximal rotating fixation structure of FIG. 36.
Figure 40:
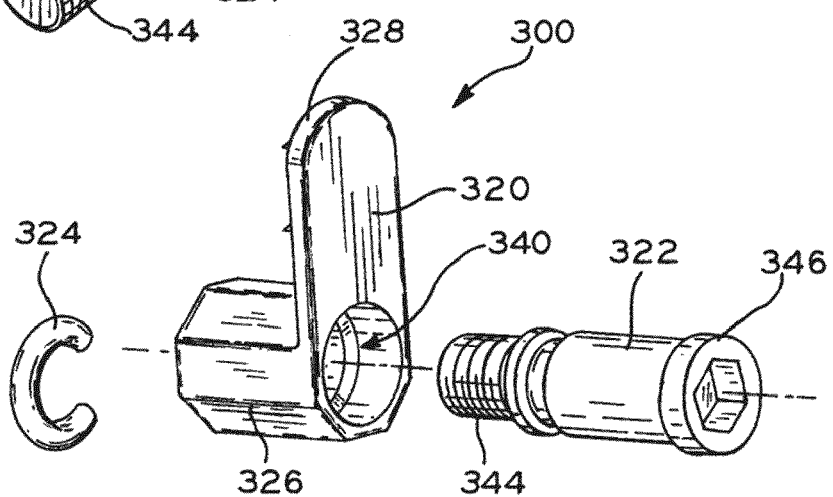
FIG. 40 is an exploded perspective view of the proximal rotating fixation structure of FIG. 36.

Proximal fixation structure 300 is illustrated in FIGS. 38-40 and includes washer 320, fastener 322, and snap ring 324. Washer 320 is an essentially L-shaped structure that includes body portion 326 and tissue engagement arm 328 that extends substantially perpendicular to body portion 326. A plurality of teeth 330 extend from washer 320, and specifically from tissue engagement arm 328 of washer 320. Teeth 330 may be arranged in various patterns. For example, teeth 330 may be aligned in columns and rows, teeth 330 may be aligned diagonally, or teeth 330 may be distributed randomly across the surface of washer 320. Adjacent teeth 330 may be separated by approximately 1 mm, 2 mm, 3 mm, or more, for example. According to an exemplary embodiment of the present disclosure, each tooth 330 includes at least one face, referred to herein as blocking face 332, that extends substantially normal to engagement arm 328 of washer 320 and/or body 82 of proximal femoral implant 80B, as discussed in more detail below. Blocking faces 332 of teeth 330 may face the same or different directions. Washer 320 includes bore 340 configured to receive fastener 322. Fastener 322 may include any suitable fastening mechanism, including an anchor or a mechanism that expands once inserted into body 82 of proximal femoral implant 80B. For example, fastener 322 may be a screw or bolt having external thread 344 and head 346, as shown in FIG. 40.

Distal fixation structure 302 is illustrated in FIGS. 41-42 and may be substantially identical to proximal fixation structure 300, described above with reference to FIGS. 38-40, except as described below. Distal fixation structure 302 includes washer 320', fastener 322', and snap ring 324'. Washer 320' is an essentially T-shaped structure that includes body portion 326' and tissue engagement arms 328' that extend substantially perpendicular to body portion 326 and in opposite directions from one another. A plurality of teeth 330' extend from washer 320', and specifically from tissue engagement arms 328' of washer 320'. In the illustrated embodiment of FIG. 37, blocking faces 332' of teeth 330' on the top tissue engagement arm 328' and blocking faces 332' of teeth 330' on the bottom tissue engagement arm 328' face in opposite directions, but it is within the scope of the present invention that blocking faces 332' of teeth 330' may face in substantially the same direction.

In operation, a surgeon may attach tissue structures to proximal femoral implant 80B. To attach a tissue structure to the medial side of proximal femoral implant 80B, the surgeon may follow the same processes described above with respect to proximal femoral implant 80 of FIGS. 13-17 and proximal femoral implant 80A of FIG. 22. For example, the surgeon may place the tissue structure in contact with porous surface 96 on medial protrusion 86 of proximal femoral implant 80B and secure the tissue structure in place by threading sutures through apertures 98 and the corresponding throughbores. To attach a tissue structure to the lateral side of proximal femoral implant 80B, the surgeon first positions the tissue structure in contact with one or more of porous surfaces 106, 106'. Next, the surgeon may clamp the tissue structure against porous surfaces 106, 106', using fixation structures 300, 302. An exemplary method of clamping the tissue structure with fixation structures 300, 302, is set forth in the following paragraphs.

Figure 43A:
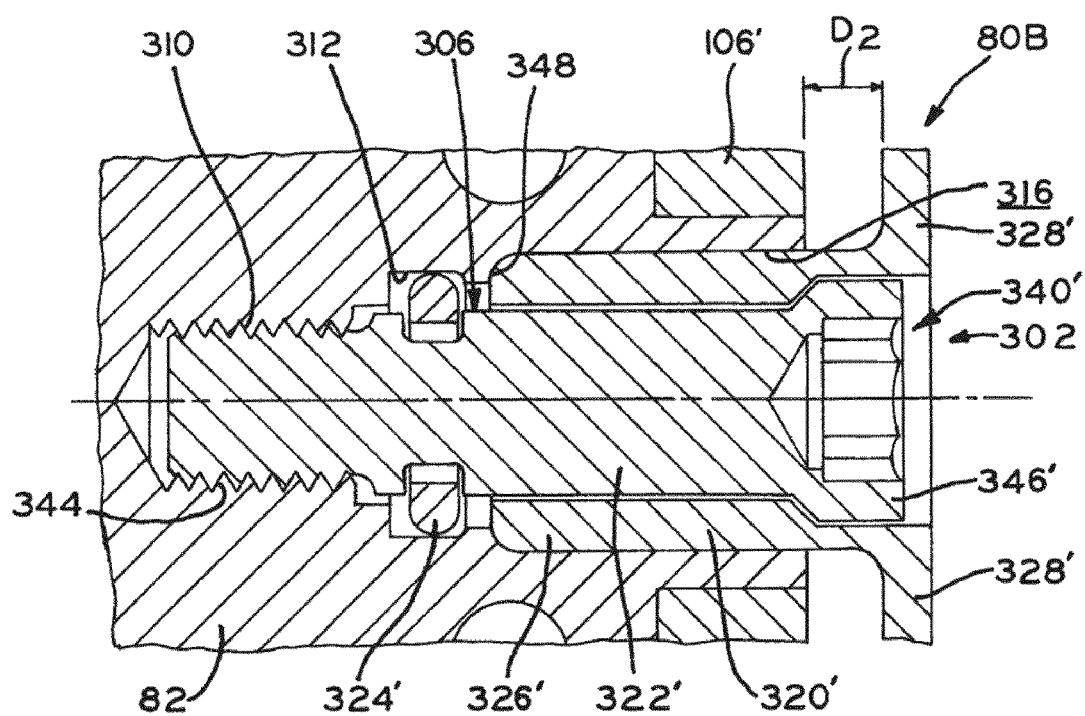
FIG. 43A is a view similar to FIG. 43 showing an alternative distal rotating fixation structure.

First, the surgeon selects desired fixation structures 300, 302, from a set provided. The set may include, for example, washers 320, 320', of various sizes and washers 320, 320', having various arrangements and sizes of teeth 330, 330'. According to an exemplary embodiment of the present disclosure, body portions 326, 326', of washers 320, 320', and/or fasteners 322, 322', may be provided in various lengths to alter the final distance between engagement arms 328, 328', of washers 320, 320', and body 82 of proximal femoral implant 80B. This distance may impact the clamping force applied by washers 320, 320', to the tissue structure and the space available for the tissue structure. Therefore, depending on the desired clamping force, the amount of tissue to be attached, and other considerations, the distance between engagement arms 328, 328', of washers 320, 320', and body 82 of proximal femoral implant 80B may vary. For example, the distance between engagement arms 328, 328', of washers 320, 320', and body 82 of proximal femoral implant 80B may vary between approximately 1 mm, 2 mm, 3 mm, 4 mm, 5 mm, 6 mm, 7 mm, 8 mm, or more. As shown in FIG. 43, the surgeon may select washer 320' having engagement arm 328' that is separated from body 82 by distance D1. If more space is desired between engagement arm 328' and body 82, the surgeon may select washer 320' having engagement arm 328' that is separated from body 82 by distance D2 which is greater than distance D1, as shown in FIG. 43A. As the distance between engagement arms 328, 328', of washers 320, 320', and body 82 increases, teeth 330, 330', may also increase in length. For example, teeth 330, 330', may be available in lengths of approximately 1 mm, 2 mm, 3 mm, 4 mm, 5 mm, 6 mm, 7 mm, 8 mm, or more.

Figure 36A:
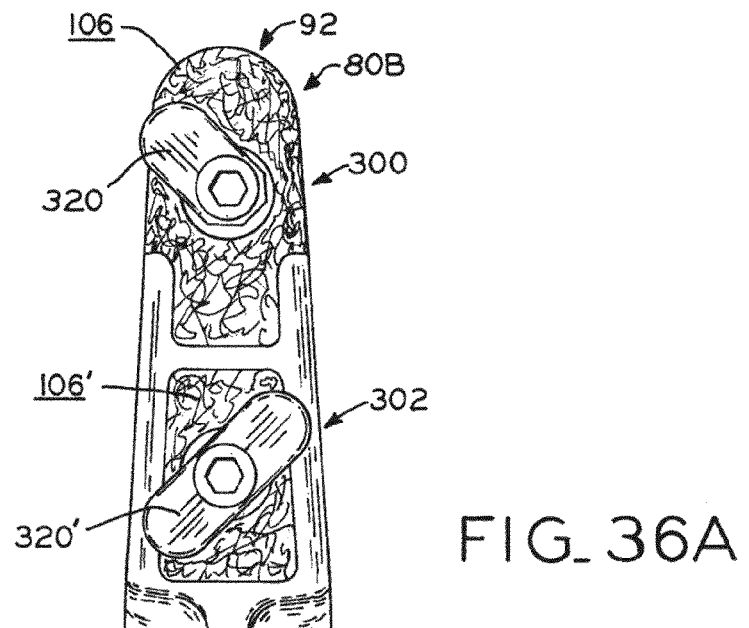
FIG. 36A is a lateral elevational view of the proximal femoral implant of FIG. 36, illustrating the proximal and distal rotating fixation structures in different positions than in FIG. 36.
Figure 37:
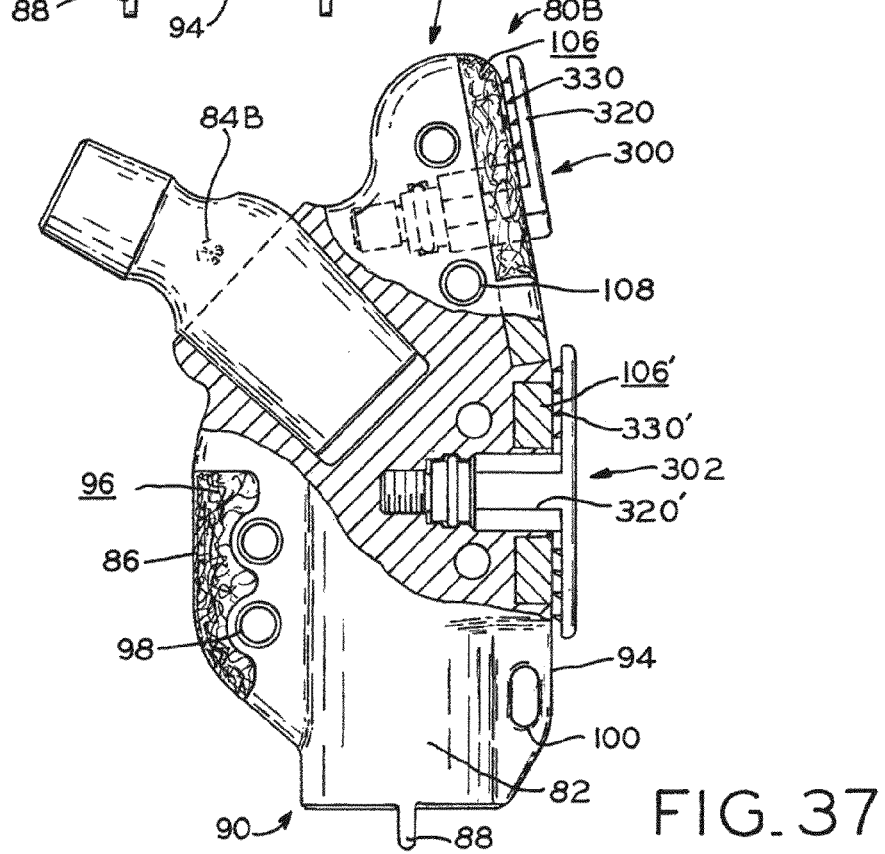
FIG. 37 is a partial cross-sectional anterior/posterior elevational view of the proximal femoral implant of FIG. 36.

Next, the surgeon aligns the selected washers 320, 320', relative to body 82 and inserts washers 320, 320', into bores 304, 306, of proximal femoral implant 80B. The surgeon may rotate washers 320, 320', at an angle relative to body 82, as shown in FIG. 36A, especially if a significant amount of tissue remains. Alternatively, the surgeon may align washers 320, 320', in a straight configuration proximally-distally relative to body 82, as shown in FIG. 36. According to an exemplary embodiment of the present disclosure, the surgeon may align washers 320, 320', to substantially cover the tissue structure with engagement arms 328, 328', of washers 320, 320'. In other words, the surgeon may align washers 320, 320', to maximize contact between engagement arms 328, 328', of washers 320, 320', and the tissue structure. For example, as shown in FIG. 36A, washers 320, 320', may be rotated side to side to follow the path of the tissue structure. According to another exemplary embodiment of the present disclosure, the surgeon may rotate washers 320, 320', to resist movement or retraction of the tissue structure with teeth 330, 330', and specifically blocking faces 332, 332', of teeth 330, 330'. Referring to FIG. 37, blocking faces 332 of teeth 330 on proximal fixation structure 300 are aligned to resist proximal movement of a tissue structure away from proximal femoral implant 80B, while blocking faces 332' of teeth 330' on distal fixation structure 302 are aligned to resist both proximal and distal movement of a tissue structure away from proximal femoral implant 80B. According to an exemplary embodiment of the present invention, blocking faces 332 of teeth 330 on proximal fixation structure 300 are aligned to resist proximal movement the gluteus medius and the gluteus minimus muscles, while blocking faces 332' of teeth 330' on distal fixation structure 302 are aligned to resist proximal movement of the gluteus maximus muscle and distal movement of a quadriceps muscle. In the illustrated embodiment of FIG. 36, each washer 320, 320', may be rotated to eight different positions due to the octagonal shape of bores 304, 306, and the corresponding octagonal shape of body portion 326, 326', of washers 320, 320'. The number of available positions may be increased or decreased by varying the shape of bores 304, 306, and washers 320, 320'.

After aligning washers 320, 320', with proximal femoral implant 80B, the surgeon secures washers 320, 320', to proximal femoral implant 80B using fasteners 322, 322', and optionally snap rings 324, 324'. Referring to the illustrated embodiment of FIG. 43, fastener 322' and snap ring 324' attached thereto are first inserted through bore 340 of washer 320' and into bore 306 in body 82 of proximal femoral implant 80B. Eventually, external thread 344' of fastener 322' engages internal thread 310 of bore 306, and snap ring 324' expands into annular indentation 312. In this arrangement, head 346' of fastener 322' prevents washer 320' from withdrawing from bore 306 and shoulder 348 of wall 316 prevents washer 320' from retracting into bore 306. Therefore, washer 320' is able to maintain a fixed axial spacing from body 82. Also, the keyed engagement between octagonal body portion 326' of washer 320' and octagonal wall 316 prevents washer 320' from spinning freely in bore 306.

Figure 44:
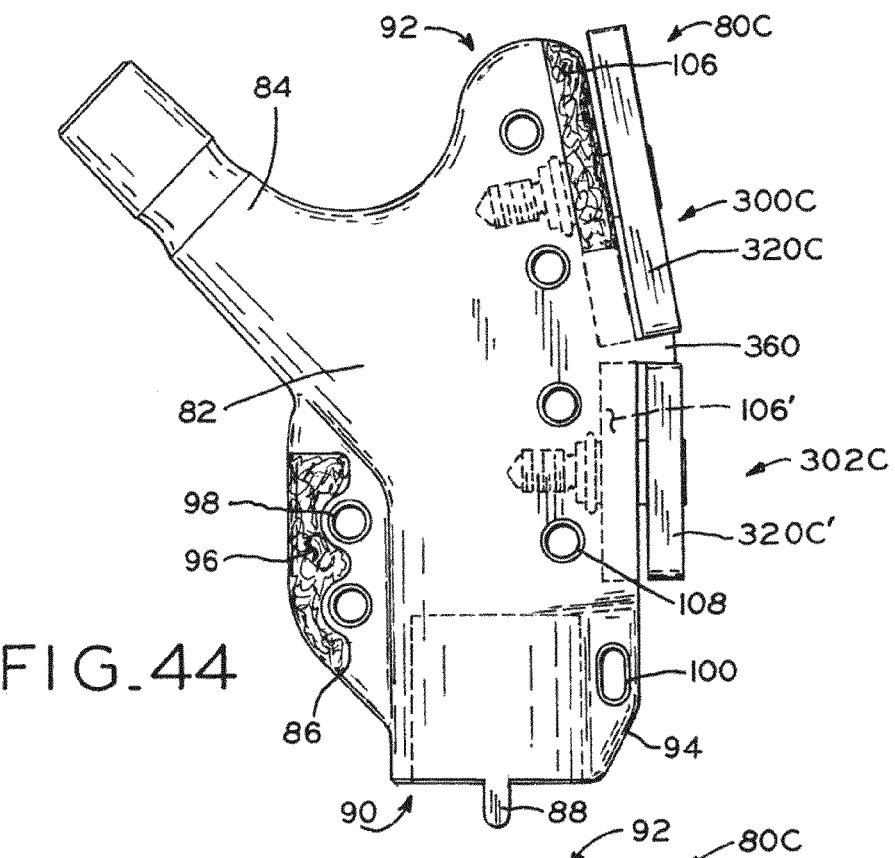
FIG. 44 is an anterior/posterior elevational view of a proximal femoral implant according to yet another exemplary embodiment of the present disclosure including a first mechanism for controlling the alignment of proximal and distal fixation structures relative to the implant.
Figure 45:
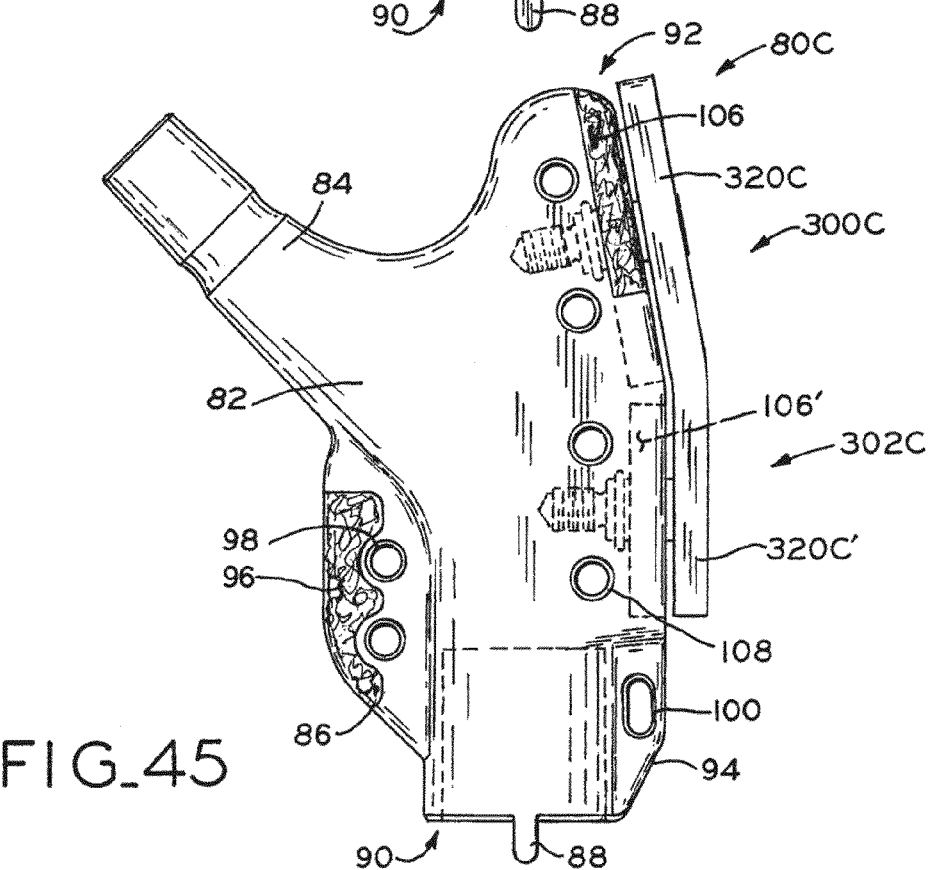
FIG. 45 is an anterior/posterior elevational view of the proximal femoral implant of FIG. 44 including a second mechanism for controlling the alignment of the proximal and distal fixation structures relative to the implant.
Figure 46:
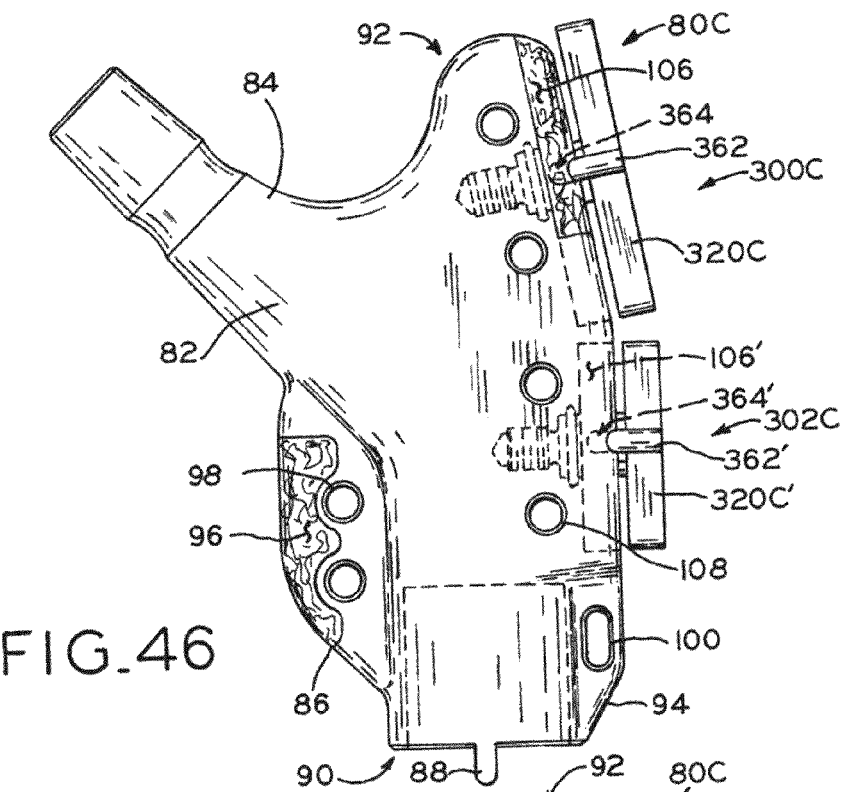
FIG. 46 is an anterior/posterior elevational view of the proximal femoral implant of FIG. 44 including a third mechanism for controlling the alignment of the proximal and distal fixation structures relative to the implant.
Figure 47:
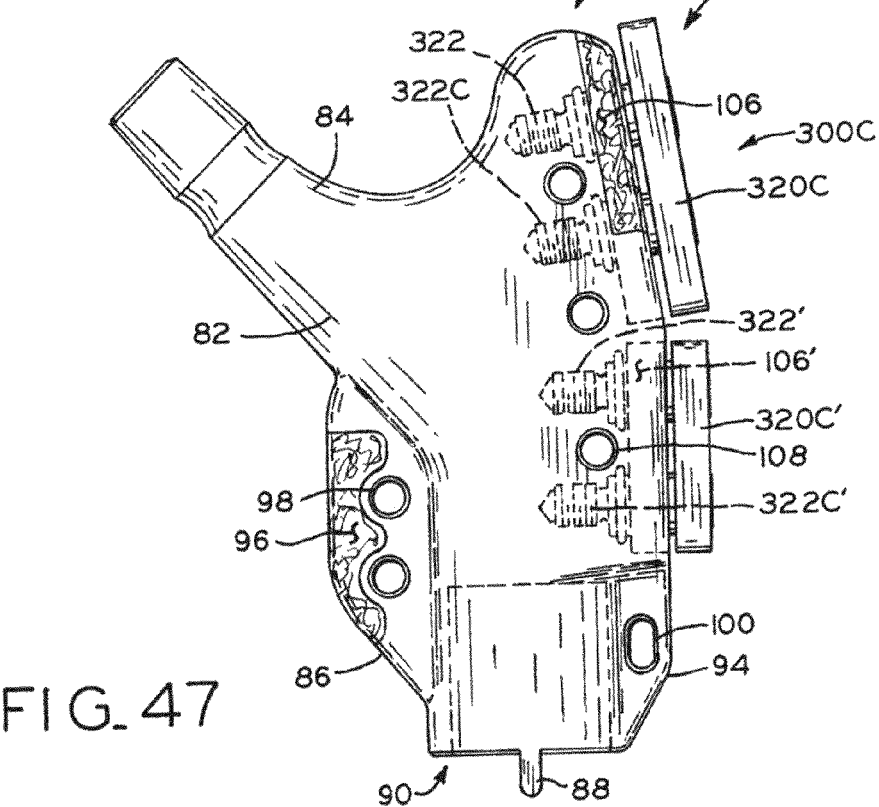
FIG. 47 is an anterior/posterior elevational view of the proximal femoral implant of FIG. 44 including a fourth mechanism for controlling the alignment of the proximal and distal fixation structures relative to the implant.

Other suitable mechanisms for maintaining the desired alignment of fixation structures 300C, 302C, relative to body 82 are illustrated in FIGS. 44-47 with respect to another proximal femoral implant 80C. Like the keyed mechanism described above with respect to washers 320, 320', of FIGS. 35-37, the mechanisms of FIGS. 44-47 may prevent washers 320C, 320C', from spinning freely relative to body 82 once the desired alignment of washers 320C, 320C', is selected. For example, the mechanisms of FIGS. 44-47 may be used to secure washers 320C, 320C', in a straight configuration proximally-distally relative to body 82 or in an angled configuration relative to body 82. As shown in FIG. 44, body 82 may include any number of protrusions 360 configured to abut washer 320C and/or washer 320C'. As shown in FIG. 45, washers 320C, 320C', may be secured together in a desired alignment to form a unitary structure. For example, washer 320C could be secured at an angle relative to washer 320C', or washers 320C, 320C', may be attached together in parallel. As shown in FIG. 46, washers 320C, 320C', may include protrusions 362, 362', configured to be received within corresponding grooves 364, 364', of body 82. As shown in FIG. 47, each washer 320C, 320C', may include more than one fastener, including fastener 322, 322', described above and an additional fastener 322C, 322C', both configured to engage body 82.

According to an exemplary embodiment of the present disclosure, the tissue structure should be held tightly in contact with porous surfaces 106, 106', of proximal femoral implant 80B, beneath washers 320, 320'. More particularly, the tissue structure should be held tightly in contact with porous surfaces 106, 106', of proximal femoral implant 80B, beneath engagement arms 328, 328', of washers 320, 320'. Thus, the bottom surfaces of engagement arms 328, 328', of washers 320, 320', act as clamping surfaces. According to another exemplary embodiment of the present disclosure, washers 320, 320', should permit adequate circulation and fluid flow through the tissue structure. For example, teeth 330, 330', on washers 320, 320', may be oriented to resist movement of the tissue structure, but adjacent teeth 330, 330', may be separated to permit blood and fluid to flow between adjacent teeth 330, 330'. Optionally, if washers 320, 320', provide too much or too little clamping pressure against the tissue structure, fixation structures 300, 302, may be removed and replaced with fixation structures 300, 302, of a different size. For example, if washers 320, 320', provide too much clamping pressure against the tissue structure, fixation structures 300, 302, may be removed and replaced with fixation structures 300, 302, having longer body portions 326, 326', and/or longer fasteners 322, 322'. Also, the attachment between the tissue structures and porous surfaces 106, 106', may be enhanced with sutures threaded through at least one aperture 108 and its associated throughbore.

Figure 48:
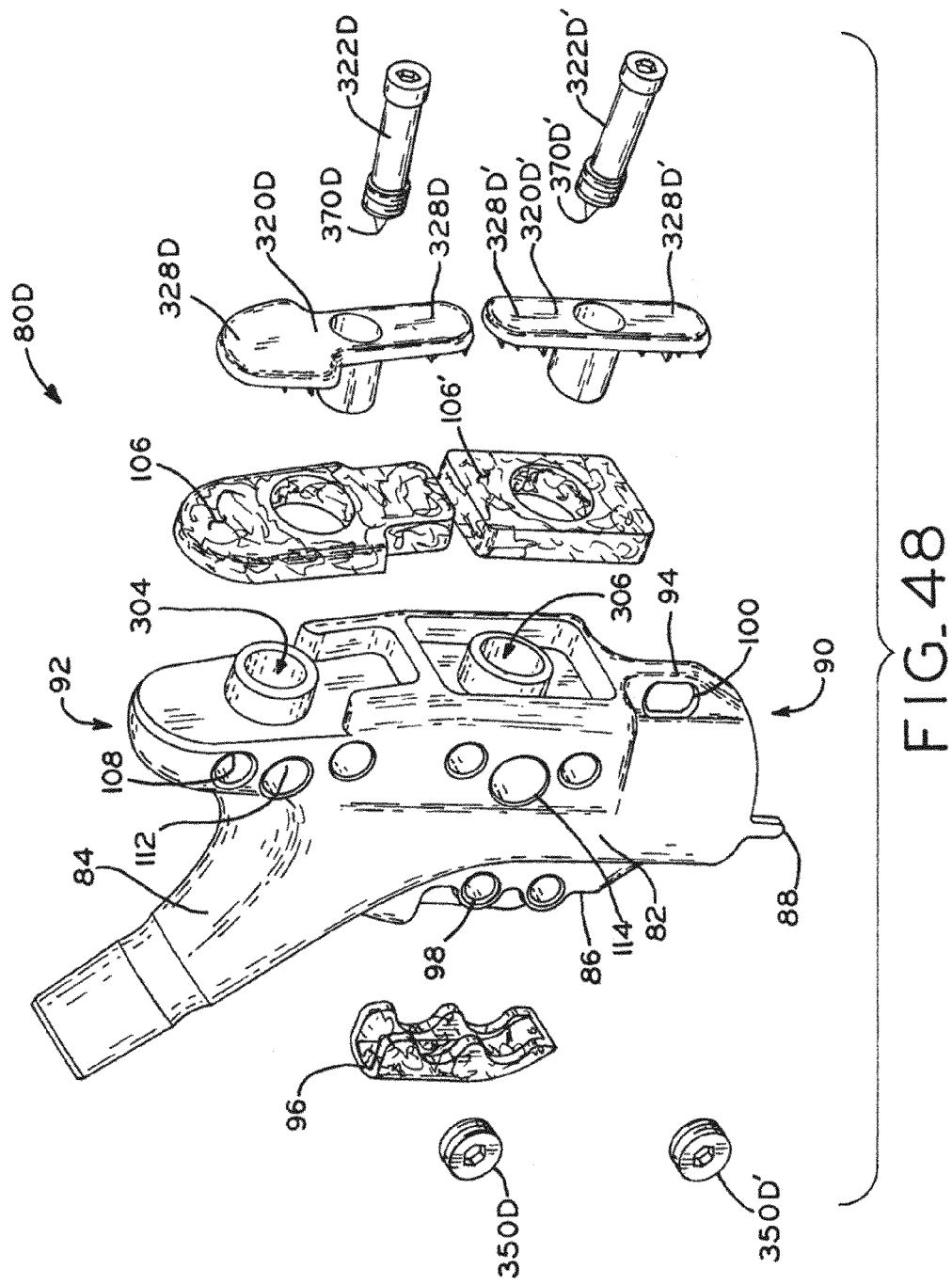
FIG. 48 is an exploded perspective view of a proximal femoral implant according to still yet another exemplary embodiment of the present disclosure including a proximal fixation structure and a distal fixation structure, each fixation structure having a washer, a fastener, and a set screw.
Figure 49:
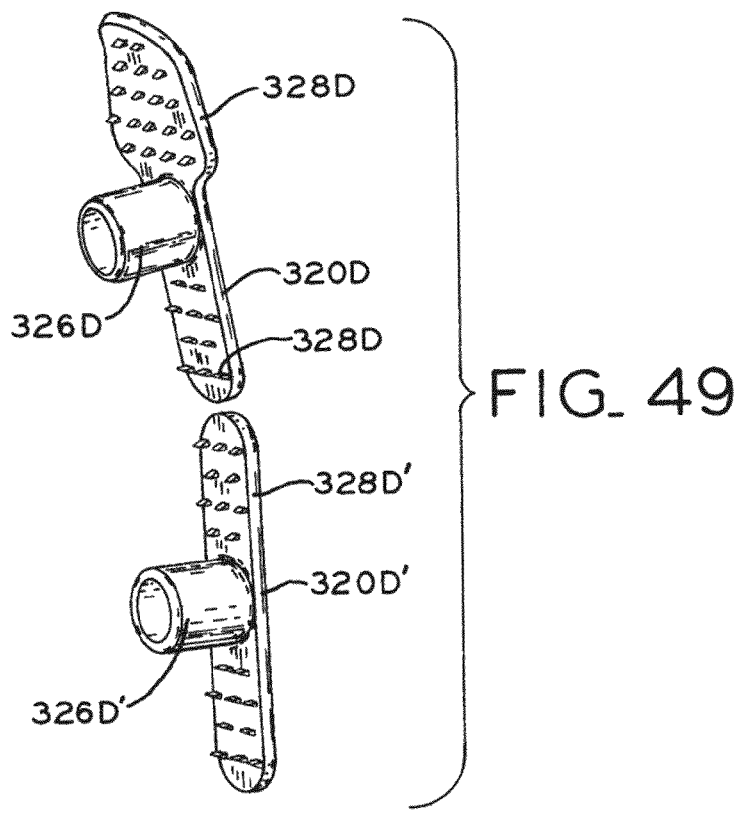
FIG. 49 is a perspective view of the proximal and distal washers of FIG. 48.
Figure 50:
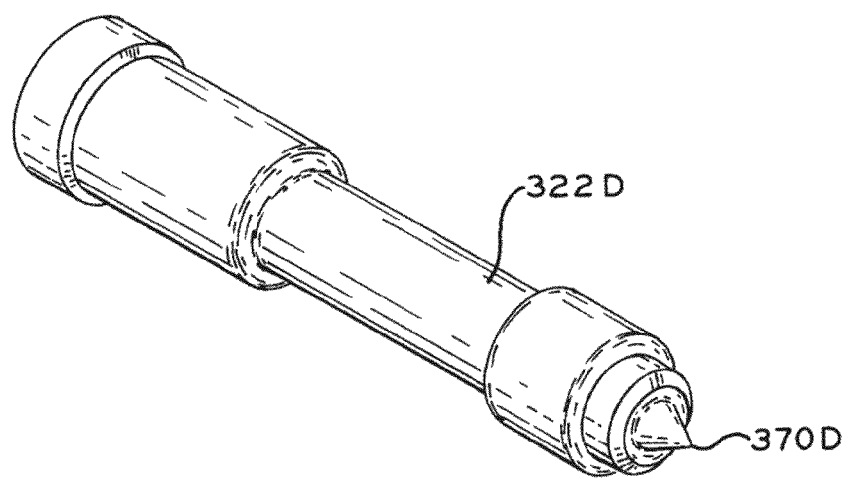
FIG. 50 is a perspective view of the fastener of FIG. 48.

Referring next to FIGS. 48-50, yet another embodiment proximal femoral implant 80D is shown and may be substantially identical to proximal femoral implant 80, described above with reference to FIGS. 13-17, proximal femoral implant 80A, described above with reference to FIG. 22, proximal femoral implant 80B, described above with reference to FIGS. 35-43, or proximal femoral implant 80C, described above with reference to FIGS. 44-47, except as described below. Proximal femoral implant 80D includes body 82, neck 84, adjustment tabs 88, medial protrusion 86, lateral protrusion 94, distal end 90, and proximal end 92. The medial side of proximal femoral implant 80D includes porous surface 96 and a plurality of apertures 98 defining throughbores in body 82. The lateral side of proximal femoral implant 80D includes porous surfaces 106, 106', and a plurality of lateral apertures 108 defining throughbores in body 82. Porous surfaces 96, 106, 106', may include porous material that is substantially identical to porous surface 45 described above. As shown in FIG. 48, porous surfaces 96, 106, 106', are inlayed and attached to body 82, such as via diffusion bonding. Body 82 of proximal femoral implant 80D also includes cross apertures 112, 114, which are described further below.

Referring still to FIGS. 48-50, proximal femoral implant 80D further includes proximal fixation structure 300D and distal fixation structure 302D. Fixation structures 300D, 302D, may be substantially identical to fixation structures 300, 302, described above with reference to FIGS. 35-43, and fixation structures 300C, 302C, described above with reference to FIGS. 35-37, except as described below. Proximal fixation structure 300D includes washer 320D, fastener 322D, and set screw 350D, and distal fixation structure 302D includes washer 320D', fastener 322D', and set screw 350D'.

Both washers 320D, 320D', are essentially T-shaped structures. Unlike proximal washer 320 of FIGS. 38-40, proximal washer 320D of FIGS. 48-49 widens at its proximal end. More particularly, tissue engagement arm 328D of proximal washer 320D widens near proximal end 92 of proximal femoral implant 80D. In this embodiment, proximal washer 320D may be configured to wrap around proximal end 92 of proximal femoral implant 80D, proximally, anteriorly, and/or posteriorly, for improved tissue attachment. Like washers 320, 320' of FIGS. 38-40, washers 320D, 320D' of FIGS. 48-49 may be configured to rotate relative to body 82. Alternatively, washers 320D, 320D', may be attached in fixed angular alignment relative to body 82. Each fastener 322D, 322D', is provided with a sharp tip 370D, 370D'.

In operation, as fasteners 322D, 322D', are inserted into body 82, tips 370D, 370D', may puncture the tissue structure that has been pulled across the lateral side of body 82. In this embodiment, the surgeon is able to pull the tissue structure to a desired tension and simultaneously insert fasteners 322D, 322D', and washers 320D, 320D'. The surgeon avoids having to cut the tissue structure with a blade and then insert fasteners 322D, 322D', and washers 320D, 320D', all while trying to maintain the desired tension of the tissue structure. Also, as shown in FIG. 48, set screws 350D, 350D', may be inserted anteriorly and/or posteriorly into cross apertures 112, 114, of body 82 to contact and secure medially extending fasteners 322D, 322D', in body 82.

Figure 51:
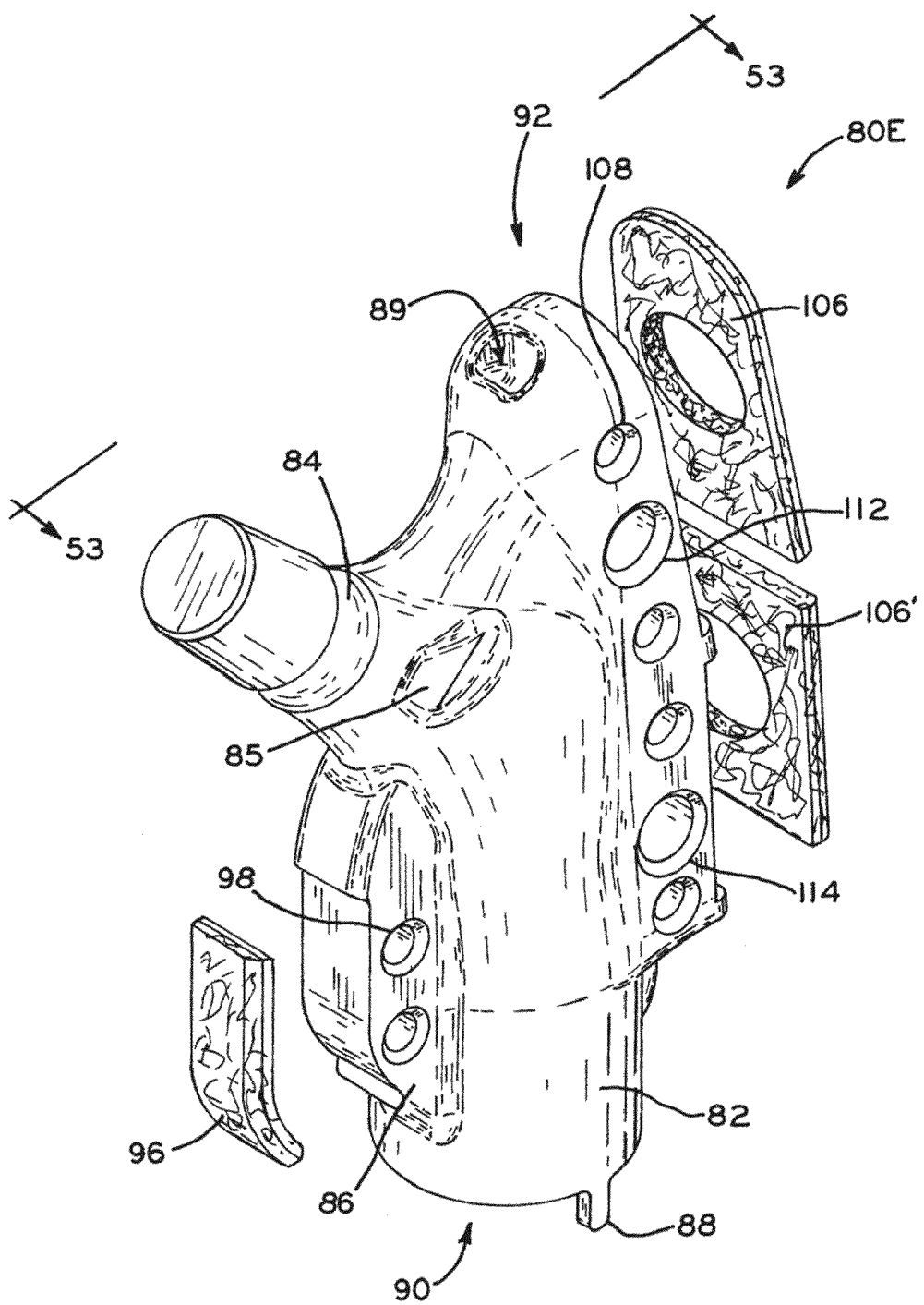
FIG. 51 is an exploded perspective view of a proximal femoral implant according to still yet another exemplary embodiment of the present disclosure.
Figure 52:
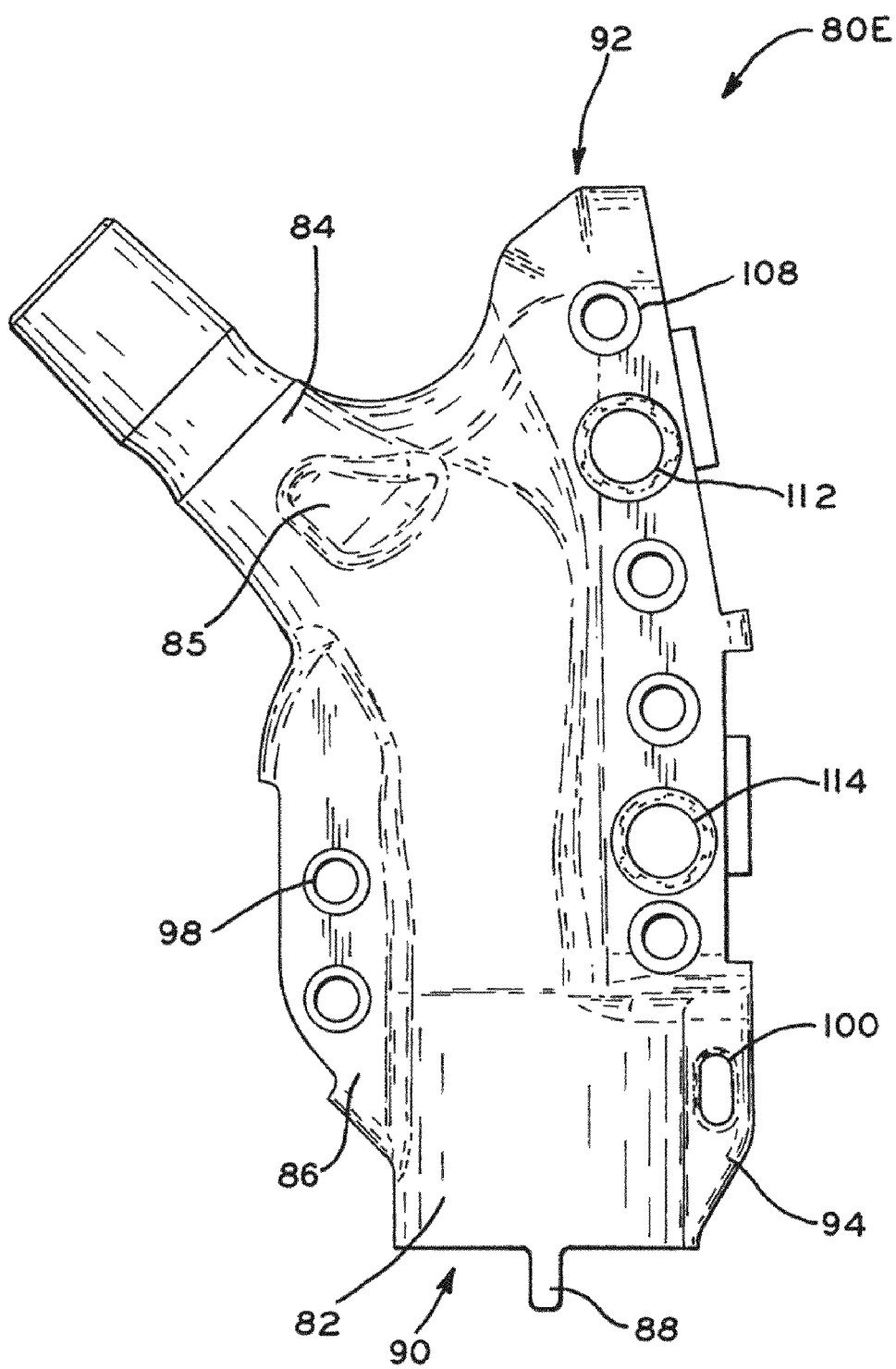
FIG. 52 is an anterior/posterior elevational view of the proximal femoral implant of FIG. 51.

Referring next to FIGS. 51-54, yet another embodiment proximal femoral implant 80E is shown and may be substantially identical to proximal femoral implant 80, described above with reference to FIGS. 13-17, proximal femoral implant 80A, described above with reference to FIG. 22, proximal femoral implant 80B, described above with reference to FIGS. 35-43, proximal femoral implant 80C, described above with reference to FIGS. 44-47, or proximal femoral implant 80D, described above with reference to FIGS. 48-50, except as described below. Proximal femoral implant 80E includes body 82, neck 84, adjustment tabs 88, medial protrusion 86, lateral protrusion 94, distal end 90, and proximal end 92. As shown in FIG. 51, neck 84 includes flats 85 to aid in gripping proximal femoral implant 80E during implantation. Also, proximal end 92 of body 82 includes recess 89 that is sized to receive an impaction tool during implantation. The medial side of proximal femoral implant 80E includes porous surface 96 and a plurality of apertures 98 defining throughbores in body 82. The lateral side of proximal femoral implant 80E includes porous surfaces 106, 106', and a plurality of lateral apertures 108 defining throughbores in body 82. Porous surfaces 96, 106, 106', may include porous material that is substantially identical to porous surface 45 described above. As shown in FIG. 51, porous surfaces 96, 106, 106', are inlayed and attached to body 82, such as via diffusion bonding. Body 82 of proximal femoral implant 80E also includes cross apertures 112, 114, which are described further below.

Figure 54:
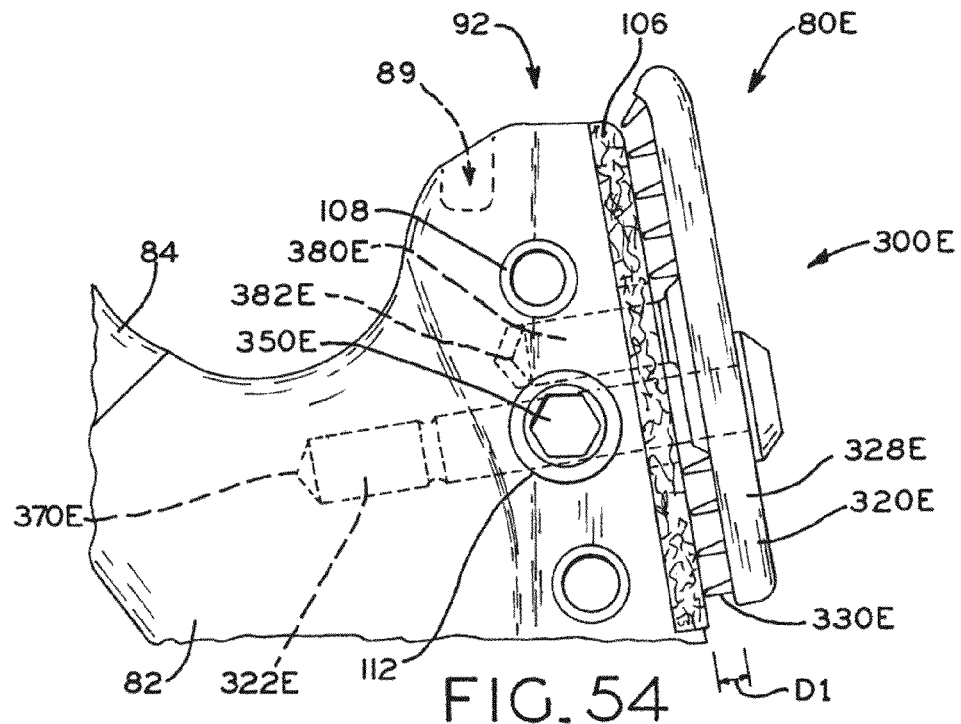
FIG. 54 is an anterior/posterior elevational view of a proximal fixation structure coupled to the proximal femoral implant of FIG. 51.

Referring to FIG. 54, proximal femoral implant 80E further includes proximal fixation structure 300E and a distal fixation structure (not shown), which may be substantially identical to fixation structures 300, 302, described above with reference to FIGS. 35-43, fixation structures 300C, 302C, described above with reference to FIGS. 35-37, or fixation structures 300D, 302D, described above with reference to FIGS. 48-50, except as described below. Proximal fixation structure 300E includes washer 320E, fastener 322E, set screw 350E, and spike 380E. As shown in FIG. 54, both fastener 322E and spike 380E have sharp, pointed tips. Specifically, fastener 322E includes sharp tip 370E and spike 380E includes sharp tip 382E.

Figure 54A:
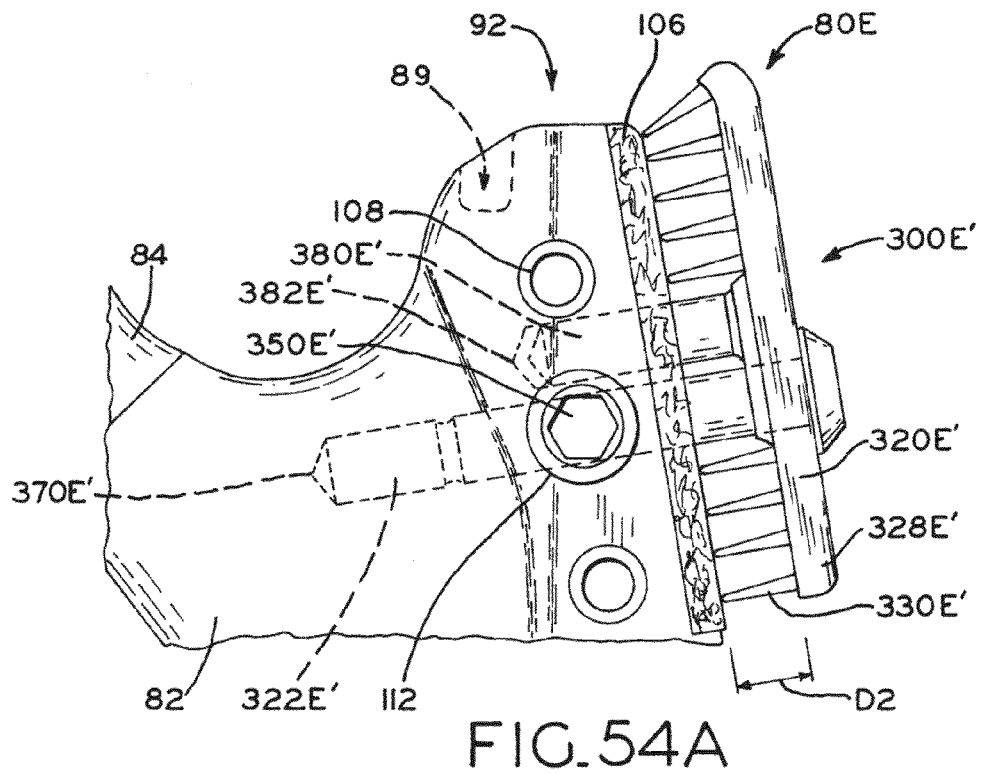
FIG. 54A is a view similar to FIG. 54 showing an alternative proximal fixation structure.

As shown by comparing FIGS. 54 and 54A, fastener 322E may be provided in various lengths to alter the final distance between engagement arms 328E of washer 320E and body 82 of proximal femoral implant 80E. This distance may impact the clamping force applied by washer 320E to the tissue structure and the space available for the tissue structure. Therefore, depending on the desired clamping force, the amount of tissue to be attached, and other considerations, the distance between engagement arms 328E of washer 320E and body 82 of proximal femoral implant 80B may vary. For example, the distance between engagement arms 328E of washer 320E and body 82 of proximal femoral implant 80B may vary between approximately 1 mm, 2 mm, 3 mm, 4 mm, 5 mm, 6 mm, 7 mm, 8 mm, or more. As shown in FIG. 54, the surgeon may select washer 320E having engagement arm 328E that is separated from body 82 by distance D1. If more space is desired between engagement arm 328E and body 82, the surgeon may select an alternative washer 320E' having engagement arms 328E' that are separated from body 82 by distance D2 which is greater than distance D1, as shown in FIG. 54A. As the distance between engagement arms 328E of washer 320E and body 82 increases, teeth 330E may also increase in length. For example, teeth 330E of FIG. 54 may have a length of approximately 4 mm or 5 mm, while teeth 330E' of FIG. 54A may have a length of approximately 7 mm or 8 mm. According to an exemplary embodiment of the present invention, a set of washers may be provided including washer 320E of FIG. 54, washer 320E' of FIG. 54A, and washers having teeth of other lengths.

Figure 53:
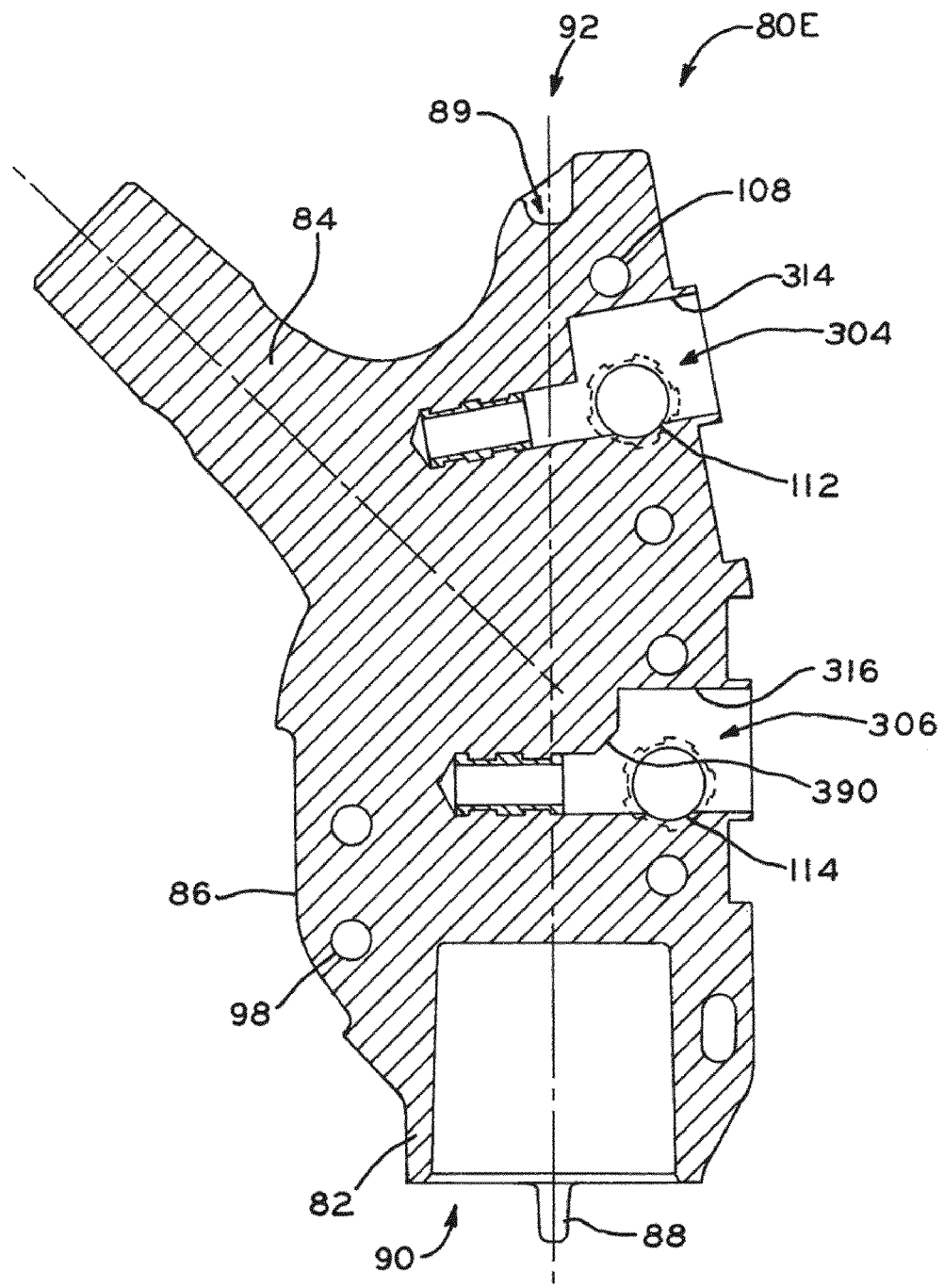
FIG. 53 is a cross-sectional view of the proximal femoral implant of FIG. 51, taken along line 53-53 of FIG. 51.

Referring to FIGS. 53 and 54, proximal femoral implant 80E includes proximal bore 304 that is sized to receive proximal fixation structure 300E and distal bore 306 that is sized to receive the distal fixation structure (not shown). For example, as shown in FIG. 54, bore 304 may be sized and shaped to receive both fastener 322E and spike 380E of proximal fixation structure 300E. It is also within the scope of the present invention that proximal femoral implant 80E may include distinct, spaced apart bores for receiving fastener 322E and spike 380E. Walls 314, 316, that define bores 304, 306, respectively, may include various features to facilitate insertion of the fixation structures. For example, as shown in FIG. 53, wall 316 that defines distal bore 306 includes chamfered portion 390. Chamfered portion 390 of wall 316 may define a conically or spherically shaped entry into distal bore 306 to guide insertion of the distal fixation structure (not shown).

In operation, as proximal fixation structure 300E and the distal fixation structure (not shown), are inserted into body 82, tip 370E of fastener 322E and tip 382E of spike 380E may puncture the tissue structure that has been pulled across the lateral side of body 82. In this embodiment, the surgeon is able to pull the tissue structure to a desired tension and simultaneously insert fastener 322E and spike 380E. The surgeon avoids having to cut the tissue structure with a blade and then insert fastener 322E and spike 380E, all while trying to maintain the desired tension of the tissue structure. Then, as shown in FIG. 54, the surgeon inserts set screw 350E anteriorly and/or posteriorly into cross aperture 112 of body 82 to contact and secure the medially extending fastener 322E. With both fastener 322E and spike 380E located within bore 304 of body 82, proximal fixation structure 300E is prevented from spinning relative to body 82.

Although the methods and apparatuses described in this disclosure describe attachment of natural tissue structures to the orthopaedic implants, the methods and apparatuses may also be used to secure artificial tissue structures to the orthopaedic implants in substantially similar manners.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A segmental tibial orthopaedic implant configured for attachment to a tissue structure, the segmental tibial orthopaedic implant comprising:
    a body comprising an anterior surface, a posterior surface, a lateral surface, a medial surface, a proximal end, and a distal end, the proximal end of the body comprising a bearing surface configured to support articulation with a distal femoral component, and the anterior surface of the body comprising a porous material; and
    at least one washer comprising a clamping surface, the at least one washer rotatably coupled to the body with the clamping surface facing the anterior surface of the body, wherein the at least one washer is configured to clamp the tissue structure between the clamping surface and the anterior surface of the body.

2. The segmental tibial orthopaedic implant of claim 1, wherein the clamping surface of the at least one washer maintains a fixed spacing from the body as the at least one washer is rotated relative to the body from a first rotational position to a second rotational position.

3. The segmental tibial orthopaedic implant of claim 1, wherein the at least one washer comprises a plurality of teeth that extend from the clamping surface toward the body to clamp the tissue structure, each tooth comprising a blocking face that extends in a direction substantially perpendicular to the body.

4. The segmental tibial orthopaedic implant of claim 1, wherein the at least one washer comprises a body portion and at least one engagement arm that extends in a direction substantially perpendicular to the body portion, the at least one engagement arm comprising the clamping surface and extending across a surface of the body of the implant when the body portion is received within the body of the implant.

5. The segmental tibial orthopaedic implant of claim 4, wherein the body defines an internally threaded bore configured to receive an externally threaded fastener configured to couple the at least one washer to the body.

6. The segmental tibial orthopaedic implant of claim 1, wherein the porous material comprises a porous pad attached to the anterior surface of the body.

7. The segmental tibial orthopaedic implant of claim 1, wherein the body defines a suture throughbore having a counterbored opening.

8. The segmental tibial orthopaedic implant of claim 1, wherein the body defines a suture throughbore and the porous material entirely surrounds an opening into the suture throughbore.

9. The segmental tibial orthopaedic implant of claim 1, wherein the body defines a curved suture throughbore that curves one of medially and laterally as the curved suture throughbore extends posteriorly from the anterior surface of the body.

10. A segmental tibial orthopaedic implant configured for attachment to a tissue structure, the segmental tibial orthopaedic implant comprising:
a body comprising an anterior surface, a posterior surface, a lateral surface, a medial surface, a proximal end, and a distal end, the proximal end of the body comprising a bearing surface configured to support articulation with a distal femoral component;
a medial washer coupled to the body, the medial washer configured to clamp a medial tissue structure against the anterior surface of the body; and
a lateral washer coupled to the body in spaced relation to the medial washer, the lateral washer configured to clamp a lateral tissue structure against the anterior surface of the body.

11. The segmental tibial orthopaedic implant of claim 10, further comprising a medial fastener and a lateral fastener, wherein the body defines a medial bore configured to receive the medial washer and the medial fastener and a lateral bore configured to receive the lateral washer and the lateral fastener.

12. The segmental tibial orthopaedic implant of claim 11, further comprising a bar, the segmental tibial orthopaedic implant having a first configuration in which the medial and lateral washers are received in the medial and lateral bores of the body and a second configuration in which the bar spans the anterior surface of the body and is received in the medial and lateral bores of the body.

13. The segmental tibial orthopaedic implant of claim 10, wherein the medial washer is coupled to the body at a first angle relative to the body to resist movement of a medial tissue structure in a first direction and the lateral washer is coupled to the body at a second angle relative to the body to resist movement of a lateral tissue structure in a second direction that differs from the first direction.

14. The segmental tibial orthopaedic implant of claim 10, wherein the medial and lateral washers are rotatably coupled to the body.

15. The segmental tibial orthopaedic implant of claim 10, wherein the medial and lateral washers comprise a plurality of teeth that extend toward the body to clamp the tissue structure, each tooth comprising a blocking face that extends in a direction substantially perpendicular to the body.

16. The segmental tibial orthopaedic implant of claim 10, wherein the anterior surface of the body comprises a porous material.

17. A segmental tibial orthopaedic implant configured for attachment to a tissue structure, the orthopaedic implant comprising:
a body comprising an anterior surface, a posterior surface, a lateral surface, a medial surface, a proximal end, and a distal end, the proximal end of the body configured for articulation with an adjacent anatomical structure, and at least one of the anterior, posterior, lateral, and medial surfaces of the body comprising a porous material; and
at least one washer rotatably coupled to the body and configured to clamp the tissue structure against the porous material of the body, the at least one washer maintaining a fixed axial spacing from the body as the at least one washer is rotated relative to the body from a first rotational position to a second rotational position.

18. The orthopaedic implant of claim 17, wherein the distal end of the body is configured to couple to one of a tibia and a femur.

19. The orthopaedic implant of claim 17, wherein the body defines a bore configured to receive the at least one washer, the bore defining a shoulder that limits axial movement of the washer into the bore.

20. The orthopaedic implant of claim 19, wherein the at least one washer comprises a non-circular body portion and the bore further defines a side wall contoured to receive the non-circular body portion of the washer.

21. The orthopaedic implant of claim 17, wherein the at least one washer comprises a plurality of teeth that extend toward the body to clamp the tissue structure, each tooth comprising at least one blocking face that extends in a direction substantially perpendicular to the body.

22. A segmental tibial orthopaedic implant configured for attachment to a tissue structure, the orthopaedic implant comprising:
a body comprising an anterior surface, a posterior surface, a lateral surface, a medial surface, a proximal end, and a distal end, the proximal end of the body configured for articulation with an adjacent anatomical structure, the body defining a bore;
a first washer comprising a first body portion and a first engagement arm, the first body portion configured to extend into the bore of the implant, the first engagement arm separated a first distance from the body of the implant when the first body portion is received in the bore and configured to clamp the tissue structure against the body of the implant;
a second washer comprising a second body portion and a second engagement arm, the second body portion configured to extend into the same bore of the implant as the first body portion of the first washer, the second engagement arm separated a second distance from the body of the implant when the second body portion is received in the bore and configured to clamp the tissue structure against the body of the implant, the second distance exceeding the first distance; and
a fastener configured to extend into the bore of the implant to couple either of the first and second washers to the body of implant.

23. The orthopaedic implant of claim 22, wherein the distal end of the body is configured to couple to one of a tibia and a femur.

24. The orthopaedic implant of claim 22, wherein the second body portion of the second washer is longer than the first body portion of the first washer.

25. The orthopaedic implant of claim 22, wherein the first washer includes a first plurality of teeth extending from the first engagement arm and the second washer includes a second plurality of teeth extending from the second engagement arm, the second plurality of teeth being longer than the first plurality of teeth.

26. The orthopaedic implant of claim 25, wherein the first plurality of teeth are less than about 5 mm in length and the second plurality of teeth are greater than about 5 mm in length.

27. The orthopaedic implant of claim 22, wherein the body defines a chamfered opening into the bore to facilitate insertion of the fastener into the bore.

28. The orthopaedic implant of claim 27, wherein the chamfered opening is arcuate to define a spherically shaped opening into the bore.

* * * * *